US010414725B2

(12) United States Patent
Bayles et al.

(10) Patent No.: US 10,414,725 B2
(45) Date of Patent: Sep. 17, 2019

(54) PYRROLOMYCINS AND METHODS OF USING THE SAME

(71) Applicant: BOARD OF REGENTS OF THE UNIVERSITY OF NEBRASKA, Lincoln, NE (US)

(72) Inventors: Kenneth Bayles, Omaha, NE (US); Rongshi Li, Omaha, NE (US); Yan Liu, Omaha, NE (US)

(73) Assignee: BOARD OF REGENTS OF THE UNIVERSITY OF NEBRASKA, Lincoln, NE (US)

( * ) Notice: Subject to any disclaimer, the term of this patent is extended or adjusted under 35 U.S.C. 154(b) by 0 days.

(21) Appl. No.: 15/743,427

(22) PCT Filed: Jul. 15, 2016

(86) PCT No.: PCT/US2016/042423
§ 371 (c)(1),
(2) Date: Jan. 10, 2018

(87) PCT Pub. No.: WO2017/011725
PCT Pub. Date: Jan. 19, 2017

(65) Prior Publication Data
US 2018/0194725 A1  Jul. 12, 2018

Related U.S. Application Data

(60) Provisional application No. 62/309,685, filed on Mar. 17, 2016, provisional application No. 62/299,588, filed on Feb. 25, 2016, provisional application No. 62/219,289, filed on Sep. 16, 2015, provisional application No. 62/193,192, filed on Jul. 16, 2015.

(51) Int. Cl.
| | |
|---|---|
| *C07D 207/34* | (2006.01) |
| *C07D 231/16* | (2006.01) |
| *C07D 233/64* | (2006.01) |
| *C07D 233/68* | (2006.01) |
| *C07D 233/90* | (2006.01) |
| *C07D 249/12* | (2006.01) |
| *C07D 207/333* | (2006.01) |
| *A61P 31/04* | (2006.01) |
| *A61P 35/00* | (2006.01) |

(52) U.S. Cl.
CPC .......... *C07D 207/34* (2013.01); *A61P 31/04* (2018.01); *A61P 35/00* (2018.01); *C07D 207/333* (2013.01); *C07D 231/16* (2013.01); *C07D 233/64* (2013.01); *C07D 233/68* (2013.01); *C07D 233/90* (2013.01); *C07D 249/12* (2013.01)

(58) Field of Classification Search
None
See application file for complete search history.

(56) References Cited

U.S. PATENT DOCUMENTS

| 4,443,466 A | 4/1984 | Karjalainen et al. |
| 4,977,275 A * | 12/1990 | Hasegawa ............ C07D 207/34 546/279.1 |

FOREIGN PATENT DOCUMENTS

| JP | 53133689 A | * | 11/1978 |
| JP | S57159763 A | | 10/1982 |
| JP | 63183562 A | * | 7/1988 |
| WO | WO-2015/101670 A2 | | 7/2015 |

OTHER PUBLICATIONS

Durham et al. Canadian Journal of Chemistry, vol. 50, 3223-3228 (Year: 1972).*
Abad-Zapatero et al., Ligand efficiency indices as guideposts for drug discovery, Drug Discov. Today, 10(7):464-9 (2005).
Aguado et al., High vancomycin MIC and complicated methicillin-susceptible *Staphylococcus aureus* bacteremia, Emerg. Infect. Dis., 17(6):1099-102 (2011).
Baell et al., New substructure filters for removal of pan assay interference compounds (PAINS) from screening libraries and for their exclusion in bioassays, J. Med. Chem., 53(7):2719-40 (2010).
Brook et al., In vitro resistance of Bacillus anthracis Sterne to doxycycline, macrolides and quinolones, Int. J. Antimicrob. Agents, 18(6):559-62 (2001).
Bush et al., Index case of fatal inhalational anthrax due to bioterrorism in the United States, N. Engl. J. Med., 345(22):1607-10 (2001).
Chambers et al., Waves of resistance: *Staphylococcus aureus* in the antibiotic era, Nat. Rev. Microbiol., 7(9):629-41 (2009).
Choe et al., In vitro development of resistance to ofloxacin and doxycycline in Bacillus anthracis Sterne, Antimicrob. Agents Chemother., 44(6):1766 (2000).
Dalvie et al., Biotransformation reactions of five-membered aromatic heterocyclic rings, Chem. Res. Toxicol., 15(3):269-99 (2002).
Dhand et al., Reduced vancomycin susceptibility among clinical *Staphylococcus aureus* isolates ('the MIC Creep'): implications for therapy, F1000 Med. Rep., 4:4 (2012).
Dolgin, Genomics uncovers microbe resistance, Nat. Med., 16(10):1054-5 (2010).
Dolgin, Sequencing of superbugs seen as key to combating their spread, Nat. Med., 16(10):1054 (2010).
Gautam et al., Irreversible binding of an anticancer compound (BI-94) to plasma proteins, Xenobiotica,, 45(10) (2015).
Gautam et al., Pharmacokinetics, protein binding and metabolism of a quinoxaline urea analog as an NF-kB inhibitor in mice and rats by LC-MS/MS, Biomed. Chromatogr., 27(7):900-9 (2013).
Gillis et al., Applications of Fluorine in Medicinal Chemistry, J. Med. Chem., 58(21):8315-59 (2015).
Hagmann, The many roles for fluorine in medicinal chemistry, J. Med. Chem., 51(15):4359-69 (2008).

(Continued)

*Primary Examiner* — Nyeemah A Grazier
(74) *Attorney, Agent, or Firm* — Marshall, Gerstein & Borun LLP

(57) ABSTRACT

Provided herein are pyrrolomycin derivatives, which can be used to modulate Mcl-1, inhibit proliferation of bacteria and pathogens, as well as to treat infectious diseases and cancers.

14 Claims, 3 Drawing Sheets

(56) References Cited

OTHER PUBLICATIONS

Hajduk, Fragment-based drug design: how big is too big?, J. Med. Chem., 49(24):6972-6 (2006).

Hiramatsu et al., Methicillin-resistant *Staphylococcus aureus* clinical strain with reduced vancomycin susceptibility, J. Antimicrob. Chemother., 40(1):135-6 (1997).

Huang et al., Kinetic analysis of bile acid sulfation by stably expressed human sulfotransferase 2A1 (SULT2A1), Xenobiotica, 40(3):184-94 (2010).

Huang et al., Metabolite profiling of praziquantel and its analogs during the analysis of in vitro metabolic stability using information-dependent acquisition on a hybrid triple quadrupole linear ion trap mass spectrometer, Drug Metab. Pharmacokinet., 25(5):487-99 (2010).

Inglesby et al., Anthrax as a biological weapon, 2002: updated recommendations for management, JAMA, 287(17):2236-52 (2002).

International Application No. PCT/US16/42423, International Search Report and Written Opinion, dated Sep. 28, 2016.

International Application No. PCT/US2016/042423, International Preliminary Report on Patentability, dated Jan. 16, 2018.

Jarvis et al., National prevalence of methicillin-resistant *Staphylococcus aureus* in inpatients at United States health care facilities, 2010, Am. J. Infect. Control., 40(3):194-200 (2012).

Kuntz et al., The maximal affinity of ligands, Proc. Natl. Acad. Sci. USA, 96(18):9997-10002 (1999).

Leuthner et al., Dalbavancin (BI-387) for the treatment of complicated skin and skin structure infection, Expert Rev. Anti Infect. Ther., 13(2):149-59 (2015).

Li, Marinopyrroles: Unique Drug Discoveries Based on Marine Natural Products, Med. Res. Rev., 36(1):169-89 (2016).

Lipinski et al., Experimental and computational approaches to estimate solubility and permeability in drug discovery and development settings, Adv. Drug Deliv. Rev., 46(1-3):3-26 (2001).

Liu et al., Marinopyrrole derivatives as potential antibiotic agents against methicillin-resistant *Staphylococcus aureus* (I), Mar. Drugs, 10(4):953-62 (2012).

Liu et al., Marinopyrrole derivatives as potential antibiotic agents against methicillin-resistant *Staphylococcus aureus* (III), Mar. Drugs, 12(5):2458-70 (2014).

Maggiore et al., Ceftaroline fosamil for treating skin and skin structure infections or community-acquired pneumonia in patients with renal insufficiency, Expert Rev. Clin. Pharamcol., 8(1):141-53 (2015).

Morata et al., New antibiotics against gram-positives: present and future indications, Curr. Opin. Pharmacol., 24:45-51 (2015).

Müller et al., Fluorine in pharmaceuticals: looking beyond intuition, Science, 317(5846):1881-6 (2007).

Pendleton et al., Clinical relevance of the ESKAPE pathogens, Expert Rev. Anti. Infect. Ther., 11(3):297-308 (2013).

Price et al., In vitro selection and characterization of Bacillus anthracis mutants with high-level resistance to ciprofloxacin, Antimicrob. Agents Chemother., 47(7):2362-5 (2003).

Pubchem, (5-Chloro-3,4-dibromo-1H-pyrrole-2-yl)(2-hydroxy-3,5-dichlorophenyl) ketone, CID 23634462, pp. 1-9 (Jan. 7, 2008).
Rice, Federal funding for the study of antimicrobial resistance in nosocomial pathogens: no ESKAPE, J. Infect. Dis., 197(8):1079-81 (2008).
Sheldrick et al., Structure of vancomycin and its complex with acetyl-D-alanyl-D-alanine, Nature, 271(5642):223-5 (1978).
Silverman et al., Inhibition of daptomycin by pulmonary surfactant: in vitro modeling and clinical impact, J. Infect. Dis., 191(12):2149-52 (2005).
Suarez et al., Structure-function characterization and optimization of a plant-derived antibacterial peptide, Antimicrob. Agents Chemother., 49(9):3847-57 (2005).
Umezu et al., Regio-selective hydroxysubstitution of fluorobenzoic acid derivatives: facile synthesis of fluorosalicylic acid derivatives, J.. Fluor. Chem., 121:97-9 (2003).
Weigel et al., A rapid antimicrobial susceptibility test for Bacillus anthracis, Antimicrob. Agents Chemother., 54(7):2793-800 (2010).
Weiss et al., Antibiotics cure anthrax in animal models, Antimicrob. Agents Chemother., 55(4):1533-42 (2011).
Williamson et al., Anthrax prophylaxis: recent advances and future directions, Front Microbiol., 6:1009 (2015).
European Patent Application No. 16825233.6, Extended European Search Report, dated Nov. 27, 2018.
Masuda et al., Pyrrolomycin group antibiotics inhibit substance P-induced release of myeloperoxidase from human polymorphonuclear leukocytes, J. Antibiot. (Tokyo):44(5):533-40 (May 1991).
Raimondi et al., Synthesis and anti-staphylococcal activity of new halogenated pyrroles related to Pyrrolomycins F, J. Heterocyclic Chem., 44(6):1407-11 (Nov. 2007).
Renneberg et al., Synthese halogenierter Benzyl- und Benzoylpyrrole, Liebigs Ann. Chem., pp. 847-52 (1993).
Schillaci et al., In vitro anti-Gram-positive and antistaphylococcal biofilm activity of newly halogenated pyrroles related to pyrrolomycins, Int. J. Antimicrob. Agents, 31(4):380-2 (Apr. 2008).
Schillaci et al., Pyrrolomycins as potential anti-staphylococcal biofilms agents, Biofouling, 26(4):433-8 (2010).

* cited by examiner

PYRROLOMYCINS AND METHODS OF USING THE SAME

BACKGROUND

Bacterial resistance to antibiotics is a widespread problem with grave implications for public health. Most bacteria have a genome that consists of a single chromosome and, consequently, replicate using a process that is simpler than mitosis or meiosis. Because bacteria can grow and divide at a rate that is much faster than that of eukaryotic cells, they can undergo evolution, i.e., natural selection, to produce a significant number of multidrug-resistant strains on a time scale that is short enough to pose a serious threat to human health worldwide. Much of the rise in multidrug-resistant bacterial strains can be attributed to the overuse and misuse of antibiotics, by patients and physicians alike. Multidrug-resistant bacterial strains may also be engineered by persons with nefarious goals, e.g., bioterrorists. Therefore, the development of new antibiotics must be an ongoing endeavor.

*Bacillus anthracis* (BA) and *Staphylococcus aureus* (SA) are important human pathogens, but for very different reasons. BA is the causative agent of anthrax, which is a serious and fatal disease, and is considered an agent of biological warfare or terrorism.[1,2] Although it holds great potential as a biological weapon of mass destruction (WMD), the intentional use of this organism to infect our population has, to date, been limited to the letter attacks in 2001. While efforts to develop better-defined vaccines to the prophylaxis of anthrax are actively ongoing, their use for administration to humans is limited and their availability is very restricted.[3] Although doxycycline and ciprofloxacin can be used to treat anthrax upon immediate administration to infected patients,[4,5] BA resistance to ciprofloxacin, doxycycline and macrolides have appeared in the literature.[6-8] Furthermore, capable terrorists can engineer the resistance to these antibiotics.

In contrast to BA, SA is one of the most common causes of infection in the U.S., attributable in large part to its propensity to become multidrug-resistant.[9,10] The Infectious Disease Society of America has classified it as one of the "ESKAPE' pathogens that can readily develop resistance to the biocidal action of antibiotics.[11,12] Currently, vancomycin is the most common first-line treatment for antibiotic-resistant SA infections.[13] However, its overutilization has resulted in an increase in vancomycin-resistant *Staphylococcus aureus* strains.[9,14-16] Further, except for the addition of the oxazolidinone linezolid[17] in 2000, the lipopeptide daptomycin[18] in 2003, and the FDA's recent approval of ceftaroline,[19] tedizolid,[20] and dalbavancin,[21] the options to treat infections caused by SA are limited. Additionally, although these recently approved and late-stage antibiotics in development may prove invaluable in combating SA resistance, these bacteria will almost inevitably develop resistance to new antibacterial agents introduced to the clinic.[22] For instance, reports of resistance to linezolid and daptomycin have quickly emerged upon their introduction. In essence, antibiotic resistance is occurring faster than new compounds can be introduced into clinical practice.

Compounding this problem is the propensity of SA to form biofilms, which are a leading cause of chronic infections in medical devices and are tolerant to most currently available antibiotics. Biofilm-growing bacteria are known to mutate at a higher frequency compared to planktonic, isogenic bacteria, and thus can more quickly undergo natural selection and gain resistance to antibiotics. Additionally, biofilms thrive under hypoxic conditions, which retards growth, metabolic activity, and protein synthesis. Thus, when bacteria are producing biofilms, they are said to be in a non-replicative, "stationary" phase. Most drugs are ineffective against bacteria in such a phase, even when their planktonic progenitors remain susceptible to the same drugs. To date, no antibiofilm agents have been made available for clinical use. Thus, there is a need for new drug for combating biofilm-related infections.

SUMMARY

Provided herein are pyrrolomycin compounds, compositions of pyrrolomycin compounds, and methods of using pyrrolomycins. Provided herein are compounds, or pharmaceutically acceptable salts thereof, of formula (I):

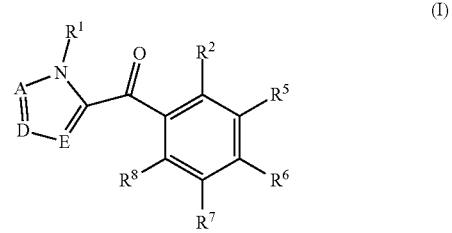

(I)

wherein $R^1$ is H, $C_{1-10}$alkyl, or $COR^9$; $R^2$ is OH, $C_{1-10}$alkoxy, $NHC(O)R^9$, or $NHSO_2R^{10}$; A and D are each $CR^3$ or N; E is $CR^4$ or N; each $R^3$ is H, halogen, $C_{1-10}$haloalkyl, $C_{1-10}$haloalkoxy, CN, $CONHR^9$, $SO_2R^{10}$, or $SO_2NHR^9$; $R^4$ is H, halogen, $C_{1-10}$haloalkyl, or $C_{1-10}$haloalkoxy; $R^5$, $R^6$, $R^7$, and $R^8$ are each H, F, Cl, $CF_3$, or $OCF_3$; $R^9$ is H, $C_{1-10}$alkyl, or $C_{6-10}$aryl; and $R^{10}$ is $C_{1-10}$alkyl or $C_{6-10}$aryl, with the proviso that (a) at least one of A, D, and E is other than N, (b) at least one $R^3$ is other than H, and (c) at least one of $R^5$, $R^6$, $R^7$, and $R^8$ is other than H. In some cases, $R^1$ is H or $C_{1-10}$alkyl. In some cases, $R^1$ is H. In various cases, $R^2$ is $NHC(O)R^9$ or $NHSO_2R^{10}$. In various cases, $R^2$ is OH or $OCH_3$. In some cases, $R^2$ is OH. In various cases, $R^3$ is halogen, $CF_3$, $OCF_3$, CN, $CONHR^9$, $SO_2R^{10}$, or $SO_2NHR^9$. In various cases, $R^3$ is $CONHR^9$, $SO_2R^{10}$, or $SO_2NHR^9$. In various cases, $R^3$ is F, Cl, or Br. In some cases, $R^3$ is F or Cl. In various cases, $R^4$ is H, halogen, $CF_3$, or $OCF_3$. In various cases, $R^4$ is F, Br, or Cl. In various cases, $R^5$ and $R^7$ are each H. In various cases, $R^6$ and $R^8$ are each independently F or Cl. In some cases, the compound has a structure selected from the group consisting of:

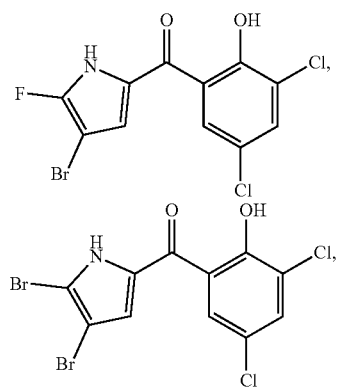

-continued
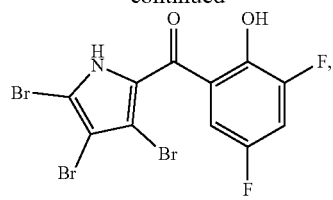
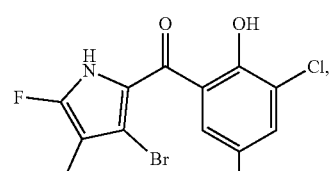
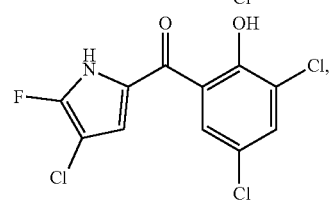
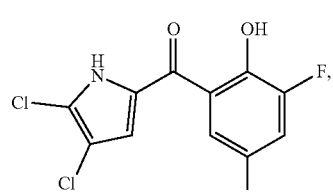
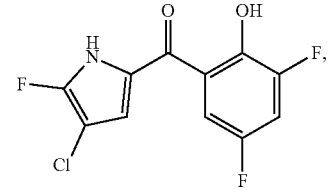
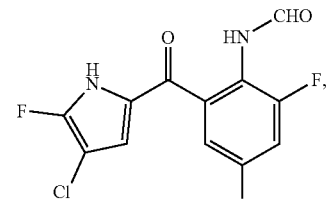
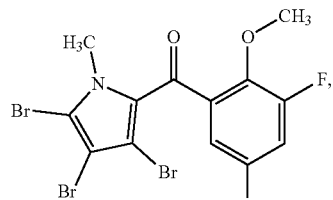
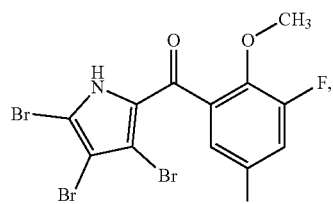
-continued
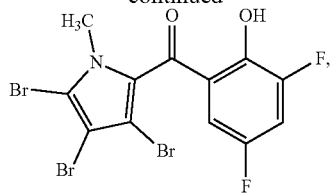
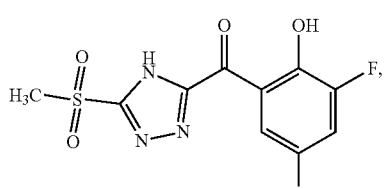
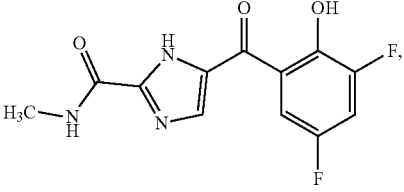
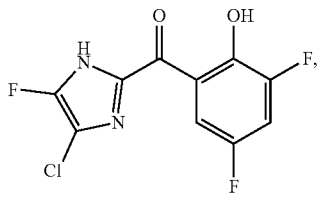
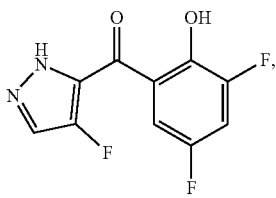
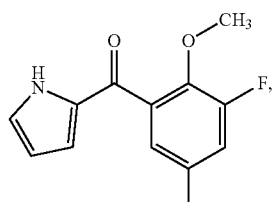
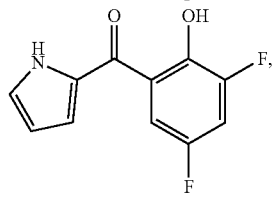
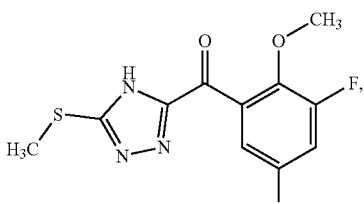

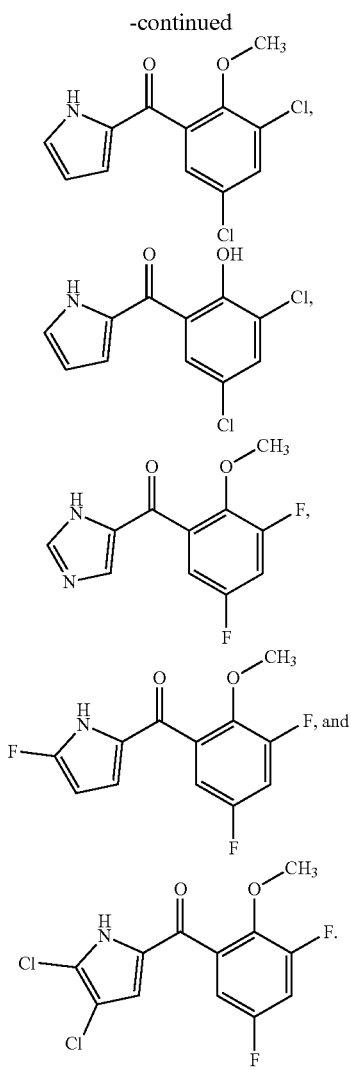

Further provided are pharmaceutical formulations comprising a compound as disclosed herein and a pharmaceutically acceptable excipient.

Also provided are methods of inhibiting the growth or proliferation of bacteria in a subject, comprising contacting the bacteria with a compound or a composition as disclosed herein in an amount sufficient to inhibit the growth or proliferation of the bacteria. In some cases, the bacteria are Gram-positive bacteria. In some cases, the bacteria are Gram-negative bacteria. In various cases, the bacteria are of a genus selected from *Staphylococcus, Enterococcus, Bacillus, Streptococcus, Klebsiella, Acinetobacter, Pseudomonas, Enterobacter, Escherichia, Clostridium, Citrobacter, Serratia, Neisseria, Corynebacterium, Cyanobacterium, Salmonella, Shigella, Helicobacter, Brucella, Borrelia, Bordetella, Bartonella, Bacteroides, Burkholderia, Mycobacterium, Mycoplasma, Campylobacter, Chlamydia, Chlamydophila, Francisella, Haemophilus, Legionella, Leptospira, Listeria, Rickettsia, Vibrio, Ureaplasma, Yersinia, Treponema, Proteus, Stenotrophomonas, Plesiomonas, Nocardia, Actinomyces, Moraxella, Erysipelothrix, Actinobacillus, Anaplasma, Pasteurella, Alcaligenes, Achromobacter,* and *Candida.*

Further provided are methods of killing a pathogen in a subject, comprising contacting the pathogen with a compound or a composition as disclosed herein in an amount sufficient to kill the pathogen. In some cases, the pathogen can be Gram-positive bacteria. In some cases, the pathogen can be Gram-negative bacteria. In various cases, the pathogen can be bacteria of a genus selected from *Staphylococcus, Enterococcus, Bacillus, Streptococcus, Klebsiella, Acinetobacter, Pseudomonas, Enterobacter, Escherichia, Clostridium, Citrobacter, Serratia, Neisseria, Corynebacterium, Cyanobacterium, Salmonella, Shigella, Helicobacter, Brucella, Borrelia, Bordetella, Bartonella, Bacteroides, Burkholderia, Mycobacterium, Mycoplasma, Campylobacter, Chlamydia, Chlamydophila, Francisella, Haemophilus, Legionella, Leptospira, Listeria, Rickettsia, Vibrio, Ureaplasma, Yersinia, Treponema, Proteus, Stenotrophomonas, Plesiomonas, Nocardia, Actinomyces, Moraxella, Erysipelothrix, Actinobacillus, Anaplasma, Pasteurella, Alcaligenes, Achromobacter,* or *Candida.*

Also provided are methods of inhibiting the growth of biofilms, comprising contacting the biofilm with a compound or a composition as disclosed herein in an amount sufficient to inhibit the growth of biofilms. In some cases, the biofilm is due to a pathogen. In some cases, the pathogen can be Gram-positive bacteria. In some cases, the pathogen can be Gram-negative bacteria. In various cases, the pathogen can be bacteria of a genus selected from *Staphylococcus, Enterococcus, Bacillus, Streptococcus, Klebsiella, Acinetobacter, Pseudomonas, Enterobacter, Escherichia, Clostridium, Citrobacter, Serratia, Neisseria, Corynebacterium, Cyanobacterium, Salmonella, Shigella, Helicobacter, Brucella, Borrelia, Bordetella, Bartonella, Bacteroides, Burkholderia, Mycobacterium, Mycoplasma, Campylobacter, Chlamydia, Chlamydophila, Francisella, Haemophilus, Legionella, Leptospira, Listeria, Rickettsia, Vibrio, Ureaplasma, Yersinia, Treponema, Proteus, Stenotrophomonas, Plesiomonas, Nocardia, Actinomyces, Moraxella, Erysipelothrix, Actinobacillus, Anaplasma, Pasteurella, Alcaligenes, Achromobacter,* or *Candida.*

The foregoing summary is not intended to define every aspect of the disclosure, and additional aspects are described in other sections, such as the Detailed Description. The entire document is intended to be related as a unified disclosure, and it should be understood that all combinations of features described herein are contemplated, even if the combination of features are not found together in the same sentence, or paragraph, or section of this document.

In addition to the foregoing, the disclosure includes, as an additional aspect, all embodiments of the disclosure narrower in scope in any way than the variations specifically mentioned above. With respect to aspects described or claimed with "a" or "an," it should be understood that these terms mean "one or more" unless context unambiguously requires a more restricted meaning. With respect to elements described as one or more within a set, it should be understood that all combinations within the set are contemplated. If aspects of the invention are described as "comprising" a feature, embodiments also are contemplated "consisting of" or "consisting essentially of" the feature.

Although the applicant(s) invented the full scope of the claims appended hereto, the claims appended hereto are not intended to encompass within their scope the prior art work of others. Therefore, in the event that statutory or judicially-recognized prior art within the scope of a claim is brought to the attention of the applicants by a Patent Office or other entity or individual, the applicant(s) reserve the right to exercise amendment rights under applicable patent laws to redefine the subject matter of such a claim to specifically exclude such prior art or obvious variations of statutory prior art from the scope of such a claim. Variations of the invention defined by such amended claims also are intended as aspects of the invention. Additional features and variations of the invention will be apparent to those skilled in the art from the entirety of this application, and all such features are intended as aspects of the invention.

DETAILED DESCRIPTION

Provided herein are compounds of formula (I) which are pyrrolomycin derivatives. The compounds disclosed herein are potent antibiofilm agents.
Compounds of Formula (I)

Figure 1:
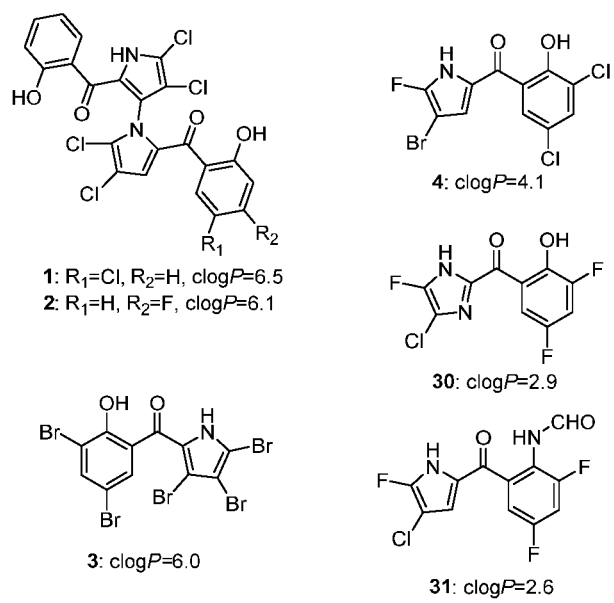
FIG. 1 shows known pyrrolomycins, their parent marinopyrroles, and bioisosteres of pyrrolomycins.

Marinopyrrole derivatives 1 and 2 (FIG. 1) have recently been reported as potent anti-methicillin resistant *Staphylococcus aureus* (MRSA) agents with MIC (minimum inhibitory concentration) values in the submicrogram/mL range.[23-25] A series of compounds called 'pyrrolomycins' were reported to have anti-Gram-positive activity, and pyrrolomycin 3 also showed antibiofilm activity with MIC in the submicrogram/mL range. Like pyrrolomycin 3, marrinopyrroles 1 and 2 have c log P values that are beyond the desired range of therapeutic drugs as stipulated by Lipinski's rule of five (R05).[26] In order to improve their physicochemical and drug-like properties, the bis-pyrrole marinopyrroles were truncated into monomers and fluorine atoms to both aromatic rings were introduced, resulting in a series of novel pyrrolomycins and their bioisosteres (4, 30, and 31 in FIG. 1) with the c log P values of up to four log units lower than those of pyrrolomycin 3 and marinopyrrole 1. These results demonstrated that novel fluorinated pyrrolomycin not only exhibited potent activity against SA with an MIC of 73 ng/mL but also showed a lack of mammalian cell cytotoxicity. Most importantly, these compounds demonstrated potent antibiofilm activity at a concentration of 8.0 µg/mL without the occurrence of bacterial resistance. In addition, novel A, B, C, D, and E Series compounds (Chart 1) have been designed to further improve the physicochemical and drug-like properties of these compounds by bioisosteric replacement of the pyrrole and dihalophenol moieties.

These results suggest that a network of hydrogen bond donor-acceptor-donor (present by the pyrrole NH-carbonyl-phenol OH) is important for anti-SA activity. Therefore, seven more series of novel pyrrolomycins and their bioisosteric replacements of both pyrrole and dihalophenol moieties were designed (Chart 1). Besides introduction of additional functional groups to both the pyrrole and benzene rings in the A1 Series, the bioisosteric replacement of the pyrrole with imidazole (B Series and C Series), pyrazole (D Series) and triazole (E Series) is investigated. The electron-withdrawing substituents on the pyrrole in A Series can stabilize the pyrrole system to avoid potential metabolic liability.[27,28] Toxicity associated with the pyrroles bearing electron-donating groups was documented. The amide (A2 series) and sulfonamide (A3 Series) are designed as surrogates for the dihalophenol moiety of the pyrrolomycins. The NH from amide or sulfonamide groups is expected to serve as a hydrogen bond donor as that of the phenol OH group. This replacement is designed to avoid the potential metabolic liability of the dihalophenol group. Fluorine atoms are incorporated since fluorinated pyrrolomycins have improved physicochemical, drug-like properties and antibacterial activities, and as fluorinated drugs often have improved bioactivities and pharmacokinetic and pharmacodynamic profiles.[29-31] These bioisosteric replacements generate new chemical entities. In turn, bioisosteric replacements are expected to alter the metabolism and improve the drug-like properties. Electron-withdrawing groups F, Cl, $CF_3$, CN, carboxamide, sulfonamide, and sulfone in the A-E Series compounds reduces the electron density and/or mask sites of the five-membered heteroaromatic rings to avoid generation of reactive metabolites by cytochrome P-450.

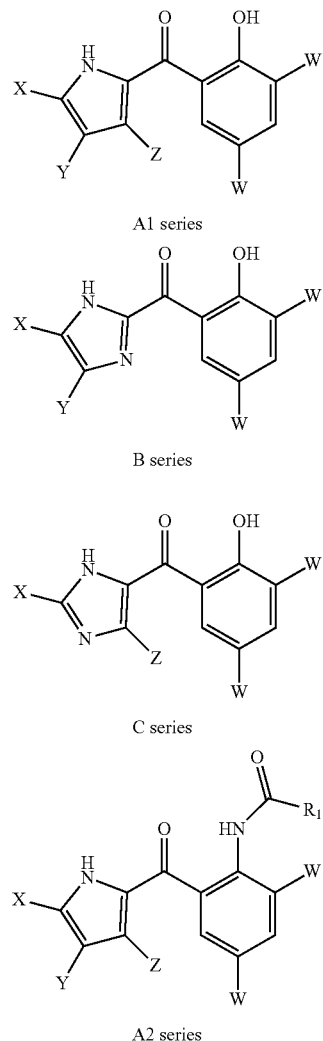

Chart 1. Novel pyrrolomycins and their bioisosteres

A1 series

B series

C series

A2 series

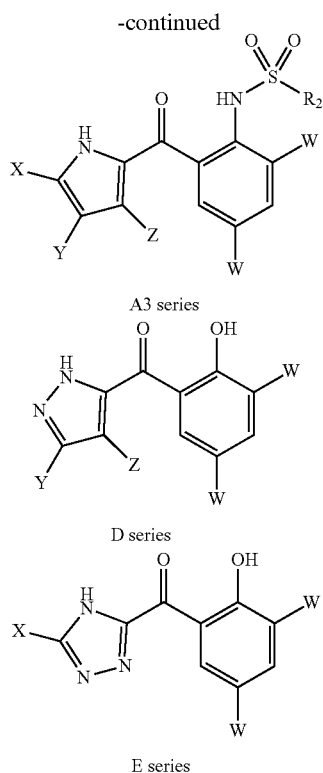

A3 series

D series

E series

X, Y, F, Cl, CF₃, CN, CONHR, SO₂R, SO₂NHR;
Z = H, F, Cl, CF₃;
W = F, Cl;
R₁ = H, alkyl, aryl;
R₂ = alkyl, aryl Thus, provided herein are compounds, or pharmaceutically acceptable salts thereof, having a structure of formula (I):

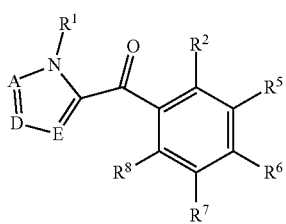

(I)

wherein $R^1$ is H, $C_{1-10}$alkyl, or $COR^9$; $R^2$ is OH, $C_{1-10}$alkoxy, $NHC(O)R^9$, or $NHSO_2R^{10}$; A and D are each $CR^3$ or N; E is $CR^4$ or N; each $R^3$ is H, halogen, $C_{1-10}$haloalkyl, $C_{1-10}$haloalkoxy, CN, $CONHR^9$, $SO_2R^{10}$, or $SO_2NHR^9$; $R^4$ is H, halogen, $C_{1-10}$haloalkyl, or $C_{1-10}$haloalkoxy; $R^5$, $R^6$, $R^7$, and $R^8$ are each H, halogen, $CF_3$, or $OCF_3$; $R^9$ is H, $C_{1-10}$alkyl, or $C_{6-10}$aryl; and $R^{10}$ is $C_{1-10}$alkyl or $C_{6-10}$aryl, with the proviso that (a) at least one of A, D, and E is other than N, (b) at least one $R^3$ is other than H, and (c) at least one of $R^5$, $R^6$, $R^7$, and $R^8$ is other than H.

As used herein, the term "$C_{1-10}$alkyl" refers to substituted or unsubstituted saturated hydrocarbon groups, including straight-chain alkyl and branched-chain alkyl groups that contain from 1 to 10 carbons in the chain, including haloalkyl groups such as trifluoromethyl and 2,2,2-trifluoroethyl, etc. $C_0$alkyl indicates a hydrogen where the group is in a terminal position, a bond if internal.

As used herein, the term "$C_{6-10}$aryl" refers to a monocyclic or polycyclic aromatic group that contains from 6 to 10 carbon atoms, preferably a monocyclic or bicyclic aromatic group, e.g., phenyl or naphthyl. Unless otherwise indicated, an aryl group can be unsubstituted or substituted with one or more, and in particular one to four groups independently selected from, for example, halogen, alkyl, alkenyl, $OCF_3$, $NO_2$, CN, NC, OH, alkoxy, amino, $CO_2H$, $CO_2$alkyl, aryl, and heteroaryl. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like. In some specific cases, the aryl can be substituted with one or more of halogen, alkyl and alkoxy.

As used herein, the term "alkoxy" refers to an alkyl group having an oxygen attached thereto. Representative alkoxy groups include methoxy, ethoxy, propoxy, tert-butoxy and the like.

As used herein, the term "haloalkyl" refers to an alkyl substituted by one or more fluorine, chlorine, bromine and/or iodine atoms. In some embodiments, the alkyl group is substituted by one, two, or three fluorine and/or chlorine atoms. In some embodiments, the haloalkyl group is a $C_{1-10}$ haloalkyl group. Non-limiting exemplary haloalkyl groups include fluoromethyl, 2-fluoroethyl, difluoromethyl, trifluoromethyl, pentafluoroethyl, 1,1-difluoroethyl, 2,2-difluoroethyl, 2,2,2-trifluoroethyl, 3,3,3-trifluoropropyl, 4,4,4-trifluorobutyl, and trichloromethyl groups.

As used herein, the term "haloalkoxy" refers to a haloalkyl attached to a terminal oxygen atom. Non-limiting exemplary haloalkoxy groups include fluoromethoxy, difluoromethoxy, trifluoromethoxy, and 2,2,2-trifluoroethoxy.

In some embodiments, A and D are each $CR^3$ and E is $CR^4$. In some embodiments, A and D are each $CR^3$, and E is N. In some embodiments, A is $CR^3$, D is N, and E is $CR^4$. In some embodiments, A is $CR^3$, and D and E are N. In some embodiments, A is N, D is $CR^3$, and E is $CR^4$. In some cases, the compound has a structure of Series A1, A2, or A3. In some cases, the compound has a structure of Series B, C, D, or E.

In some embodiments, $R^3$ is halogen, $CF_3$, $OCF_3$, CN, $CONHR^9$, $SO_2R^{10}$, or $SO_2NHR^9$. In some embodiments, $R^3$ is $CONHR^9$, $SO_2R^{10}$, or $SO_2NHR^9$. In some embodiments, $R^3$ is F, Cl, or Br. In some embodiments, $R^3$ is F or Cl.

In some embodiments, $R^4$ is H, halogen, $CF_3$, or $OCF_3$. In some cases, $R^4$ is F or Cl.

In some embodiments, $R^2$ is $NHC(O)R^9$ or $NHSO_2R^{10}$. In some embodiments, $R^2$ is OH or $OCH_3$. In some embodiments, $R^2$ is OH.

In some embodiments, $R^1$ is H or $C_{1-10}$alkyl. In some embodiments, $R^1$ is H.

In some embodiments, $R^6$ and $R^8$ are each H. In some embodiments, $R^7$ and $R^9$ are each independently F or Cl.

Specifically contemplated compounds include:

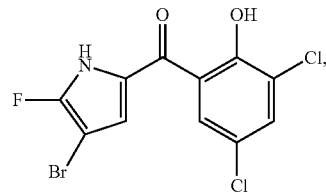

-continued
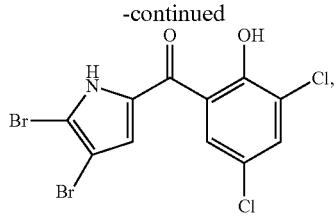
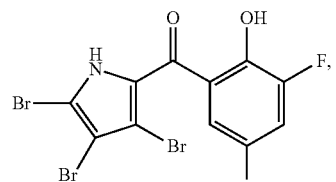
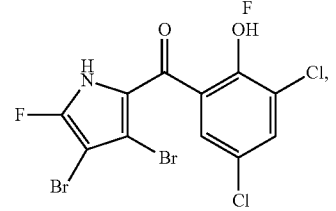
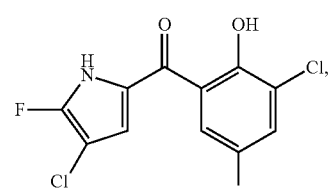
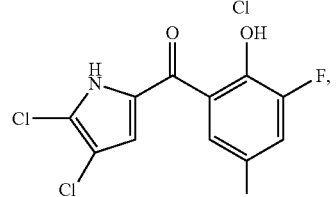
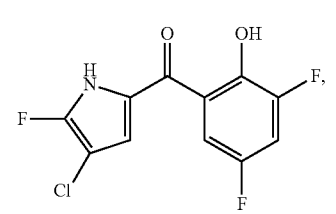
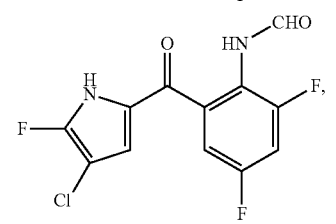
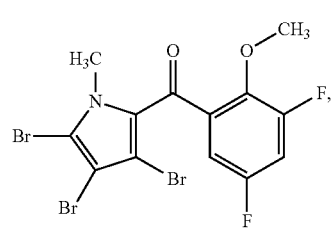
-continued
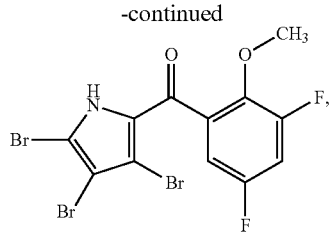
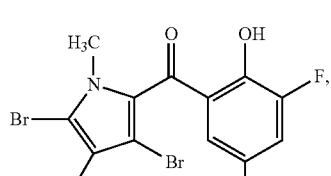
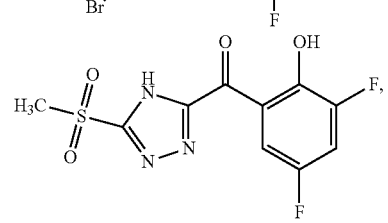
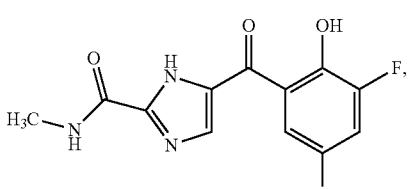
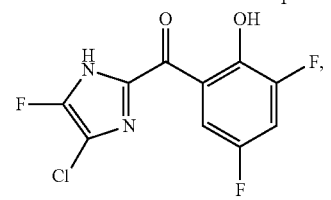
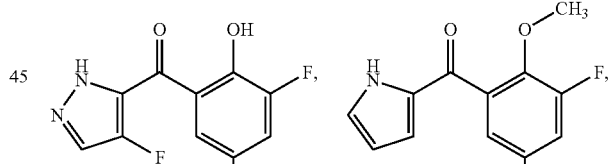
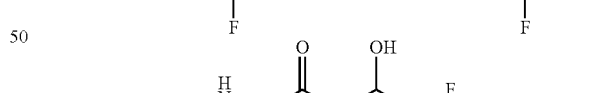
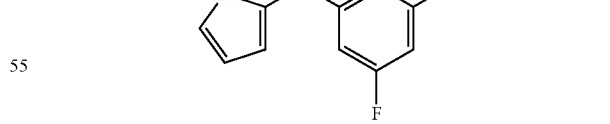
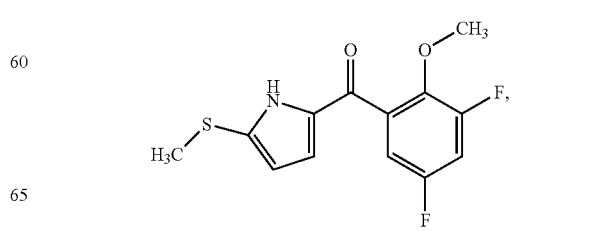

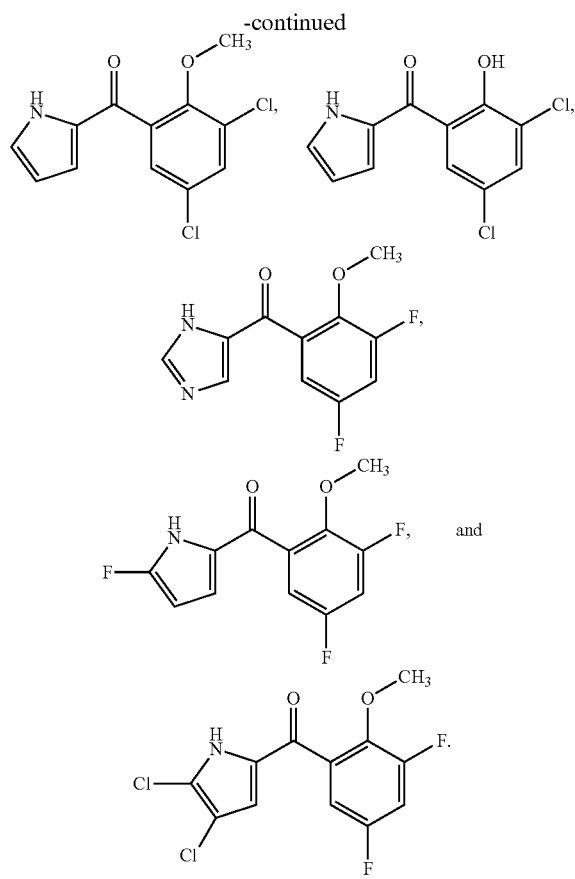

The compounds described herein also include pharmaceutically acceptable salts of the compounds disclosed herein. As used herein, the term "pharmaceutically acceptable salt" refers to a salt formed by the addition of a pharmaceutically acceptable acid or base to a compound disclosed herein. As used herein, the phrase "pharmaceutically acceptable" refers to a substance that is acceptable for use in pharmaceutical applications from a toxicological perspective and does not adversely interact with the active ingredient. Pharmaceutically acceptable salts, including mono- and bi-salts, include, but are not limited to, those derived from organic and inorganic acids such as, but not limited to, acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids. Lists of suitable salts are found in Remington's Pharmaceutical Sciences, 17th ed., Mack Publishing Company, Easton, Pa., 1985, p. 1418; Journal of Pharmaceutical Science, 66, 2 (1977); and "Pharmaceutical Salts: Properties, Selection, and Use A Handbook; Wermuth, C. G. and Stahl, P. H. (eds.) Verlag Helvetica Chimica Acta, Zurich, 2002 [ISBN 3-906390-26-8.

Synthesis of Compounds of Formula (I)

Compounds disclosed herein can be prepared in a variety of ways using commercially available starting materials, compounds known in the literature, or from readily prepared intermediates, by employing standard synthetic methods and procedures either known to those skilled in the art, or in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., March's Advanced Organic Chemistry: Reactions, Mechanisms, and Structure, $5^{th}$ edition, John Wiley & Sons: New York, 2001; and Greene, T. W., Wuts, P. G. M., Protective Groups in Organic Synthesis, $3^{rd}$ edition, John Wiley & Sons: New York, 1999, are useful and recognized reference textbooks of organic synthesis known to those in the art. The following descriptions of synthetic methods are designed to illustrate, but not to limit, general procedures for the preparation of compounds of the present invention.

The synthetic processes disclosed herein can tolerate a wide variety of functional groups; therefore various substituted starting materials can be used. The processes generally provide the desired final compound at or near the end of the overall process, although it may be desirable in certain instances to further convert the compound to a pharmaceutically acceptable salt, ester or prodrug thereof.

Scheme 1 provides representative syntheses of azolepyrrolomycin bioisosteres. Protection of a commercially available pyrazole 20 with t-butyldimethylsilyl (TBS) furnishes 21. Transmetalation of tributylstannyl pyrazole 21 with butyllithium (BuLi) at −78° C. provides a corresponding lithiated species that reacts with aldehyde 22 to yield alcohol 23. Oxidation of 23 using 2-iodoxybenzoic acid (IBX) followed by removal of TBS-protecting groups furnishes 25. Similarly, the corresponding imidazole and triazole precursors, 26 and 28, yield final compounds 27 and 29, respectively.

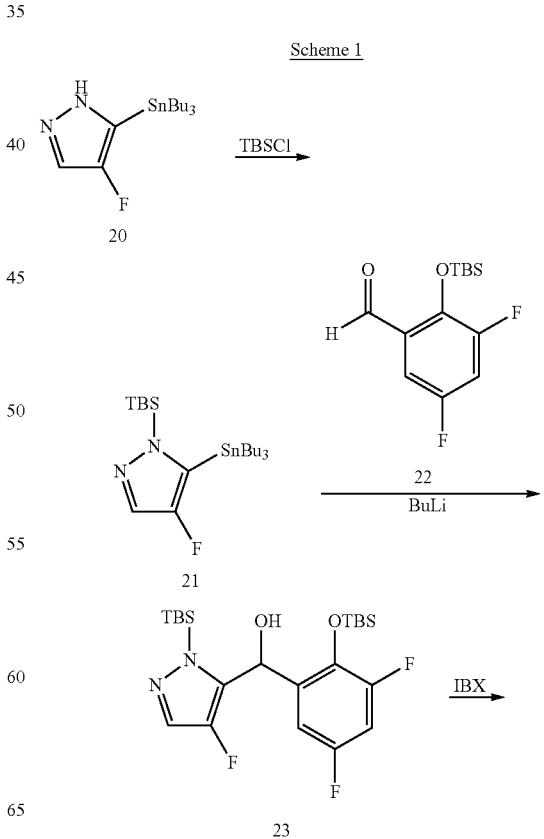

Scheme 1

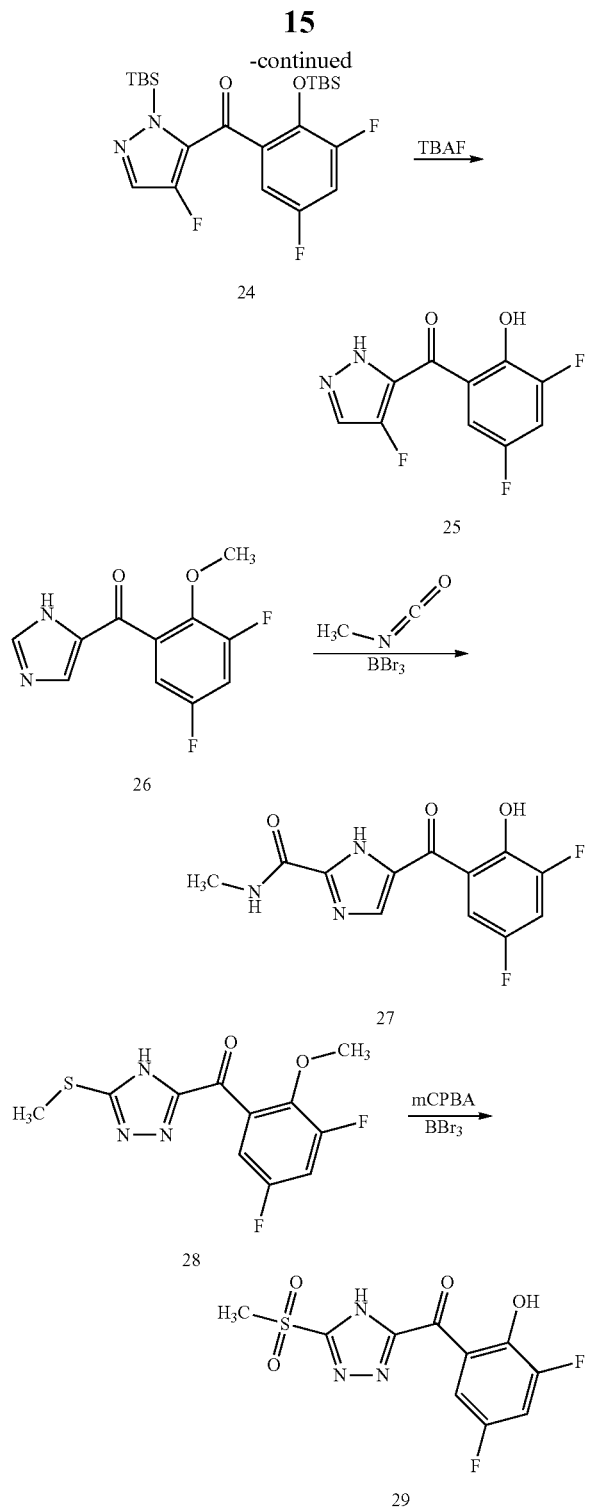

Pharmaceutical Formulations, Dosing, and Routes of Administration

Compounds disclosed herein can be formulated into a pharmaceutical formulation using a pharmaceutically acceptable excipient. The formulation can include a therapeutically effective amount of the compound.

The terms "therapeutically effective amount" and "prophylactically effective amount," as used herein, refer to an amount of a compound sufficient to treat, ameliorate, or prevent the identified disease or condition, or to exhibit a detectable therapeutic, prophylactic, or inhibitory effect. The effect can be detected by, for example, an improvement in clinical condition, reduction in symptoms, or by any of the assays or clinical diagnostic tests described herein. The precise effective amount for a subject will depend upon the subject's body weight, size, and health; the nature and extent of the condition; and the therapeutic or combination of therapeutics selected for administration. Therapeutically and prophylactically effective amounts for a given situation can be determined by routine experimentation that is within the skill and judgment of the clinician.

Dosages of the therapeutic can alternately be administered as a dose measured in mg/kg. Contemplated mg/kg doses of the disclosed therapeutics include about 0.001 mg/kg to about 1000 mg/kg. Specific ranges of doses in mg/kg include about 0.1 mg/kg to about 500 mg/kg, about 0.5 mg/kg to about 200 mg/kg, about 1 mg/kg to about 100 mg/kg, about 2 mg/kg to about 50 mg/kg, and about 5 mg/kg to about 30 mg/kg.

As herein, the compounds described herein may be formulated in pharmaceutical compositions with a pharmaceutically acceptable excipient, carrier, or diluent. The compound or composition comprising the compound is administered by any route that permits treatment of the disease or condition. One route of administration is oral administration. Additionally, the compound or composition comprising the compound may be delivered to a patient using any standard route of administration, including parenterally, such as intravenously, intraperitoneally, intrapulmonary, subcutaneously or intramuscularly, intrathecally, topically, transdermally, rectally, orally, nasally or by inhalation. Slow release formulations may also be prepared from the agents described herein in order to achieve a controlled release of the active agent in contact with the body fluids in the gastro intestinal tract, and to provide a substantial constant and effective level of the active agent in the blood plasma. The compound may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

Administration may take the form of single dose administration, or a compound as disclosed herein can be administered over a period of time, either in divided doses or in a continuous-release formulation or administration method (e.g., a pump). However the compounds of the embodiments are administered to the subject, the amounts of compound administered and the route of administration chosen should be selected to permit efficacious treatment of the disease condition.

In an embodiment, the pharmaceutical compositions are formulated with one or more pharmaceutically acceptable excipient, such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, the pH is adjusted to a range from about pH 5.0 to about pH 8. More particularly, the pharmaceutical compositions may comprise a therapeutically or prophylactically effective amount of at least one compound as described herein, together with one or more pharmaceutically acceptable excipients. Optionally, the pharmaceutical compositions may comprise a combination of the compounds described herein, or may include a second active ingredient useful in the treatment or prevention of bacterial infection (e.g., anti-bacterial or anti-microbial agents.

Formulations, e.g., for parenteral or oral administration, are most typically solids, liquid solutions, emulsions or suspensions, while inhalable formulations for pulmonary administration are generally liquids or powders. A pharmaceutical composition can also be formulated as a lyophilized solid that is reconstituted with a physiologically compatible solvent prior to administration. Alternative pharmaceutical compositions may be formulated as syrups, creams, ointments, tablets, and the like.

The term "pharmaceutically acceptable excipient" refers to an excipient for administration of a pharmaceutical agent, such as the compounds described herein. The term refers to any pharmaceutical excipient that may be administered without undue toxicity.

Pharmaceutically acceptable excipients are determined in part by the particular composition being administered, as well as by the particular method used to administer the composition. Accordingly, there exists a wide variety of suitable formulations of pharmaceutical compositions (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants (e.g., ascorbic acid), chelating agents (e.g., EDTA), carbohydrates (e.g., dextrin, hydroxyalkylcellulose, and/or hydroxyalkylmethylcellulose), stearic acid, liquids (e.g., oils, water, saline, glycerol and/or ethanol) wetting or emulsifying agents, pH buffering substances, and the like. Liposomes are also included within the definition of pharmaceutically acceptable excipients.

The pharmaceutical compositions described herein are formulated in any form suitable for an intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as cross-linked povidone, maize starch, or alginic acid; binding agents, such as povidone, starch, gelatin or acacia; and lubricating agents, such as magnesium stearate, stearic acid or talc.

Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules wherein the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions may be formulated as suspensions comprising a compound of the embodiments in admixture with at least one pharmaceutically acceptable excipient suitable for the manufacture of a suspension.

In yet another embodiment, pharmaceutical compositions may be formulated as dispersible powders and granules suitable for preparation of a suspension by the addition of suitable excipients.

Excipients suitable for use in connection with suspensions include suspending agents (e.g., sodium carboxymethylcellulose, methylcellulose, hydroxypropyl methylcellulose, sodium alginate, polyvinylpyrrolidone, gum tragacanth, gum acacia); dispersing or wetting agents (e.g., a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycethanol), a condensation product of ethylene oxide with a partial ester derived from a fatty acid and a hexitol anhydride (e.g., polyoxyethylene sorbitan monooleate)); and thickening agents (e.g., carbomer, beeswax, hard paraffin or cetyl alcohol). The suspensions may also contain one or more preservatives (e.g., acetic acid, methyl or n-propyl p-hydroxy-benzoate); one or more coloring agents; one or more flavoring agents; and one or more sweetening agents such as sucrose or saccharin.

The pharmaceutical compositions may also be in the form of oil-in water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions may be in the form of a sterile injectable preparation, such as a sterile injectable aqueous emulsion or oleaginous suspension. This emulsion or suspension may be formulated by a person of ordinary skill in the art using those suitable dispersing or wetting agents and suspending agents, including those mentioned above. The sterile injectable preparation may also be a sterile injectable solution or suspension in a non-toxic parenterally acceptable diluent or solvent, such as a solution in 1,2-propane-diol.

The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids (e.g., oleic acid) may likewise be used in the preparation of injectables.

To obtain a stable water-soluble dose form of a pharmaceutical composition, a pharmaceutically acceptable salt of a compound described herein may be dissolved in an aqueous solution of an organic or inorganic acid, such as 0.3 M solution of succinic acid, or more preferably, citric acid. If a soluble salt form is not available, the compound may be dissolved in a suitable co-solvent or combination of co-solvents. Examples of suitable co-solvents include alcohol, propylene glycol, polyethylene glycol 300, polysorbate 80, glycerin and the like in concentrations ranging from about 0 to about 60% of the total volume. In one embodiment, the active compound is dissolved in DMSO and diluted with water.

The pharmaceutical composition may also be in the form of a solution of a salt form of the active ingredient in an appropriate aqueous vehicle, such as water or isotonic saline or dextrose solution. Also contemplated are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In some embodiments, the compounds described herein may be formulated for oral administration in a lipid-based formulation suitable for low solubility compounds. Lipid-based formulations can generally enhance the oral bioavailability of such compounds.

As such, pharmaceutical compositions comprise a therapeutically or prophylactically effective amount of a compound described herein, together with at least one pharmaceutically acceptable excipient selected from the group consisting of medium chain fatty acids and propylene glycol esters thereof (e.g., propylene glycol esters of edible fatty acids, such as caprylic and capric fatty acids) and pharmaceutically acceptable surfactants, such as polyoxyl 40 hydrogenated castor oil.

In some embodiments, cyclodextrins may be added as aqueous solubility enhancers. Exemplary cyclodextrins include hydroxypropyl, hydroxyethyl, glucosyl, maltosyl and maltotriosyl derivatives of α-, β-, and γ-cyclodextrin. A specific cyclodextrin solubility enhancer is hydroxypropyl-o-cyclodextrin (BPBC), which may be added to any of the above-described compositions to further improve the aqueous solubility characteristics of the compounds of the embodiments. In one embodiment, the composition comprises about 0.1% to about 20% hydroxypropyl-o-cyclodextrin, more preferably about 1% to about 15% hydroxypropyl-o-cyclodextrin, and even more preferably from about 2.5% to about 10% hydroxypropyl-o-cyclodextrin. The amount of solubility enhancer employed will depend on the amount of the compound of the invention in the composition.

Methods of Use

The compounds disclosed herein can modulate Mcl-1 activity. The compounds disclosed herein are capable of inhibiting growth or proliferation of a pathogen, or bacteria. Thus, provided herein are methods of killing a pathogen in a subject by contacting the pathogen or bacteria with a compound or formulation as disclosed herein. In some cases, the pathogen can be Gram-positive bacteria or Gram-negative bacteria. Some specifically contemplated bacteria include *Staphylococcus, Enterococcus, Bacillus, Streptococcus, Klebsiella, Acinetobacter, Pseudomonas, Enterobacter, Escherichia, Clostridium, Citrobacter, Serratia, Neisseria, Corynebacterium, Cyanobacterium, Salmonella, Shigella, Helicobacter, Brucella, Borrelia, Bordetella, Bartonella, Bacteroides, Burkholderia, Mycobacterium, Mycoplasma, Campylobacter, Chlamydia, Chlamydophila, Francisella, Haemophilus, Legionella, Leptospira, Listeria, Rickettsia, Vibrio, Ureaplasma, Yersinia, Treponema, Proteus, Stenotrophomonas, Plesiomonas, Nocardia, Actinomyces, Moraxella, Erysipelothrix, Actinobacillus, Anaplasma, Pasteurella, Alcaligenes, Achromobacter*, and *Candida*. In various embodiments, the pathogen is methicillin-resistant, carbapenem-resistant, fluoroquinone-resistant, vancomycin-resistant, or multidrug-resistant.

The compounds disclosed herein can inhibit the growth of biofilms. The compounds disclosed herein can treat an infectious disease, and/or be used as an antibiotic.

As used herein, the term "infectious disease" refer to a condition in which an infectious organism or agent is present in a detectable amount in the blood or in a normally sterile tissue or normally sterile compartment of a subject. Infectious organisms and agents include viruses, bacteria, fungi, and parasites. The terms encompass both acute and chronic infections, as well as sepsis.

The methods disclosed herein can be for a cell, or for an organism. In some cases, the method is practiced on a mammal, e.g., a human.

Aspects described as methods of treatment should also be understood to include first or subsequent "medical use" aspects of the invention or "Swiss use" of compositions for the manufacture of a medicament for treatment of the same disease or condition.

EXAMPLES

General Experimental Procedures.

All chemicals and solvents were purchased from commercial suppliers and used without further purification. Melting points were determined on a Stanford Research Systems EZ-Melt apparatus and are uncorrected. Flash column chromatography was performed on silica gel 60, with a mesh size of 0.040-0.063 mm (EMD chemicals, Billerica, Mass., USA). $^1$H NMR (500 MHz) and $^{13}$C NMR (125 MHz) spectra were recorded on a Bruker advance III at ambient temperature. High-resolution mass spectra were obtained by electrospray ionization. Analytical HPLC was performed on an Agilent 1260 Infinity with diode array detectors and auto samplers. Preparative HPLC was performed on a Shimadzu LC-20A series. All target compounds after HPLC purification (preparative C18 column, 5 μm, 150×21.2 mm and analytical C18 column, 5 μm, 150×4.6 mm, UV 214 nm and 254 nm) possessed purities of 95%.

Example 1

Synthesis of Novel Pyrrolomycin Derivatives.

Synthesis of Compounds 8 and 9

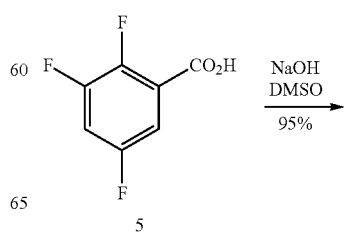

5

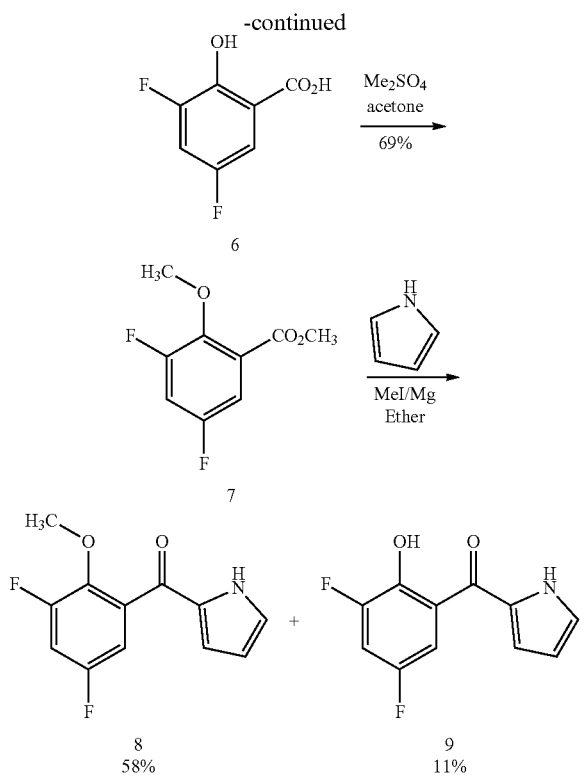

Compound 8.

Step A: After a mixture of 2,3,5-trifluorobenzoic acid (5 g, 28.4 mmol), NaOH (4.5 g, 112.5 mmol) and anhydrous DMSO (60 mL) was stirred at 130° C. for 3 h, the reaction mixture was poured into ice water (200 mL), acidified to ~pH 1, and extracted with ether (3×100 mL). The organic layer was washed with brine, dried over anhydrous MgSO$_4$, filtered and evaporated to give a crude product, 3,5-difluorosalicylic acid 6 as a white solid (4.7 g, 95%). $^1$H NMR (500 MHz, CDCl$_3$) δ 10.22 (s, 1H), 7.41 (ddd, J=8.0, 3.0, 2.0 Hz, 1H), 7.15 (dd, J=9.0, 3.0 Hz, 1H). Step B: To a solution of 6 (6.6 g, 37.9 mmol) in acetone (80 mL) were added K$_2$CO$_3$ (15 g, 108.7 mmol) and dimethyl sulfate (10 mL, 105.6 mmol). The resulting mixture was refluxed for 18 h, cooled to room temperature, and solvent was evaporated. The residue was partitioned between ether and water. The organic layer was washed with 1N NaOH solution and brine, dried over anhydrous MgSO$_4$, filtered and evaporated to dryness. The crude product was purified by silica gel column chromatography (4% ethyl acetate in hexane) to afford the desired product as a white solid 7 (5.3 g, 69%). $^1$H NMR (500 MHz, CDCl$_3$) δ 7.28 (ddd, J=8.5, 3.0, 2.0 Hz, 1H), 7.02 (dd, J=9.0, 3.5 Hz, 1H), 3.94 (d, J=0.9 Hz, 3H), 3.92 (s, 3H). Step C: A solution of methyl iodide (CH$_3$I, 1.24 mL, 19.9 mmol) in ether (10 mL) was added dropwise to a stirred magnesium turning (0.45 g, 18.8 mmol) in ether (5 mL) to maintain a gentle reflux. After the mixture was stirred for 0.5 h at room temperature, pyrrole (1.50 mL, 20.0 mmol) was added dropwise to maintain a gentle reflux. The resulting mixture was refluxed for 0.5 h and cooled to room temperature. To the pyrrylmagnesium iodide was added dropwise a solution of 7 (2.0 g, 9.9 mmol) in ether (40 mL). After stirred at room temperature for 2 h, the reaction mixture was quenched with saturated NH$_4$Cl solution and extracted with ether (3×100 mL). The organic layer was washed with brine, dried over anhydrous MgSO$_4$, filtered and evaporated to dryness. The residue was purified by silica gel column chromatography (9% ethyl acetate in hexane) to afford the desired product 8 as a brown solid (1.36 g, 58%). mp 85.7-87.1° C. $^1$H NMR (500 MHz, CDCl$_3$) δ 10.65 (s, 1H), 7.22-7.16 (m, 1H), 7.02-6.91 (m, 2H), 6.71-6.66 (m, 1H), 6.32-6.25 (m, 1H), 3.87 (d, J=1.3 Hz, 3H); $^{13}$C NMR (125 MHz, CDCl$_3$) δ 182.05 (dd, J=3.2, 2.0 Hz), 157.34 (dd, J=245.6, 11.0 Hz), 155.71 (dd, J=250.8, 11.9 Hz), 142.39 (dd, J=12.0, 3.9 Hz), 135.36 (dd, J=7.8, 2.5 Hz), 131.69 (s), 127.49 (s), 121.57 (s), 111.59 (s), 111.27 (dd, J=23.8, 3.7 Hz), 106.95 (dd, J=26.6, 23.2 Hz), 62.89 (dd, J=4.6, 0.6 Hz); HRMS (EI-TOF) M$^+$ calcd for C$_{12}$H$_9$F$_2$NO$_2$ 237.0601, found 237.0603; HPLC purity, 95.6%.

Compound 9.

After silica gel column purification of the reaction mixture above and purification by preparative HPLC, a demethylated byproduct 9 was obtained as a yellow solid (0.25 g, 11%). mp 161.7-162.5° C. $^1$H NMR (500 MHz, CDCl$_3$) δ 11.50 (s, 1H), 9.56 (s, 1H), 7.59-7.51 (m, 1H), 7.25-7.18 (m, 1H), 7.14-7.06 (m, 2H), 6.47-6.41 (m, 1H); $^{13}$C NMR (125 MHz, CDCl$_3$) δ 184.92 (t, J=2.9 Hz), 153.88 (dd, J=241.3, 10.4 Hz), 151.80 (dd, J=251.4, 11.6 Hz), 147.46 (dd, J=12.6, 3.1 Hz), 129.74 (s), 126.85 (s), 120.59 (dd, J=7.8, 4.0 Hz), 120.42 (s), 112.49 (s), 111.49 (dd, J=23.7, 4.0 Hz), 110.03 (dd, J=27.1, 21.3 Hz); HRMS (EI-TOF) M$^+$ calcd for C$_{11}$H$_7$F$_2$NO$_2$ 223.0445, found 223.0444; HPLC purity, 100%.

Synthesis of Compound 10

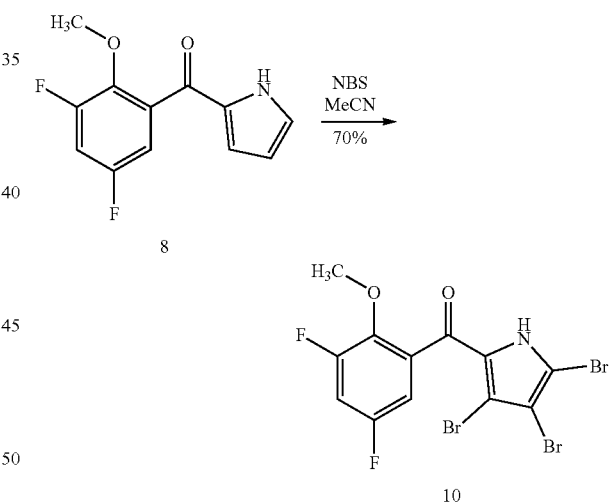

To a solution of 8 (100 mg, 0.42 mmol) in acetonitrile (2 mL) was added N-bromosuccinimide (NBS, 225 mg, 1.27 mmol) at 0° C. The resulting mixture was stirred at room temperature for 20 h and evaporated to dryness. The residue was partitioned between ether and water. The organic layer was washed with brine, dried over anhydrous MgSO$_4$, filtered and evaporated. The residue was purified by silica gel column chromatography (5% ethyl acetate in hexane) to afford 10 as a white solid (140 mg, 70%). mp 178.9-179.7° C. $^1$H NMR (500 MHz, Acetone-d$_6$) δ 12.37 (s, 1H), 7.26 (ddd, J=11.6, 8.5, 3.0 Hz, 1H), 7.06 (ddd, J=7.9, 2.8, 1.8 Hz, 1H), 3.83 (d, J=1.5 Hz, 3H). $^{13}$C NMR (125 MHz, Acetone-d$_6$) δ 180.48 (dd, J=3.5, 2.1 Hz), 158.53 (dd, J=244.8, 11.1 Hz), 156.00 (dd, J=250.7, 12.2 Hz), 142.65 (dd, J=12.0, 3.9

Hz), 135.48 (dd, J=8.4, 2.9 Hz), 131.22 (s), 111.35 (s), 111.24 (dd, J=24.3, 3.7 Hz), 108.18 (s), 107.68 (dd, J=27.0, 23.4 Hz), 106.19 (s), 62.58 (d, J=5.1 Hz); HRMS (EI-TOF) M$^+$ calcd for $C_{12}H_6Br_3F_2NO_2$ 470.7917, found 470.7919; HPLC purity, 100%.

Synthesis of Compound 3

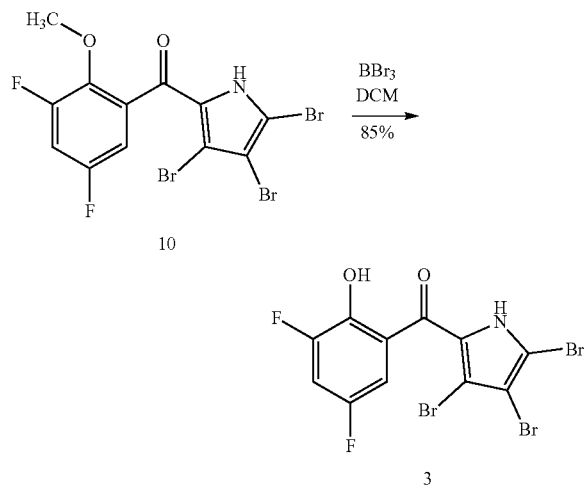

To a solution of 10 (60 mg, 0.13 mmol) in $CH_2Cl_2$ (3 mL) was added a solution of boron tribromide (BBr$_3$, 0.38 mL, 1M solution in $CH_2Cl_2$) dropwise at −78° C. The resulting mixture was stirred at this temperature for 2 h, quenched with water and extracted with $CH_2Cl_2$. The organic layer was washed with brine, dried over anhydrous MgSO$_4$, filtered and evaporated to dryness. The residue was purified by silica gel column chromatography (6% ethyl acetate in hexane) to afford the desired product as a yellow solid. This compound was purified by preparative HPLC to yield 50 mg (85%): mp 151.8-152.7° C. $^1$H NMR (500 MHz, Acetone-d$_6$) δ 12.35 (s, 1H), 9.47 (s, 1H), 7.38-7.23 (m, 1H), 7.19-7.06 (m, 1H); $^{13}$C NMR (125 MHz, Acetone-d$_6$) δ 182.50 (dd, J=3.3, 2.3 Hz), 155.58 (dd, J=240.1, 10.5 Hz), 152.17 (dd, J=245.2, 11.8 Hz), 142.44 (dd, J=14.9, 3.1 Hz), 131.19 (s), 127.47 (dd, J=8.1, 3.0 Hz), 112.18 (dd, J=24.2, 3.9 Hz), 110.47 (s), 108.26 (dd, J=27.3, 22.5 Hz), 107.64 (s), 106.11 (s); HRMS [M+H]$^+$ calcd for $C_{11}H_5Br_3F_2NO_2$ 457.7838, found 457.7852; HPLC purity, 98.6%.

Synthesis of Compound 11

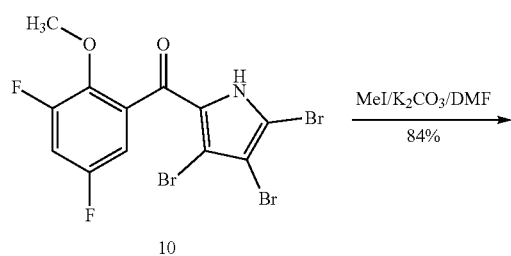

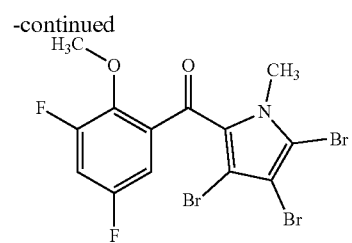

To a solution of 10 (63 mg, 0.133 mmol) in DMF (1.0 mL) at room temperature were added K$_2$CO$_3$ (55 mg, 0.40 mmol) and iodomethane (0.083 mL, 1.33 mol). The resulting mixture was stirred at room temperature for 3 h, and evaporated to dryness. The residue was partitioned between ether and water. The organic layer was washed with brine, dried over anhydrous MgSO$_4$, filtered and evaporated to afford 11 as a white solid (55 mg, 84%). This compound was purified by preparative HPLC. mp 107.4-108.1° C. $^1$H NMR (500 MHz, CDCl$_3$) δ 6.99 (ddd, J=11.2, 8.1, 3.0 Hz, 1H), 6.83 (ddd, J=7.6, 2.9, 1.7 Hz, 1H), 4.01 (s, 3H), 3.85 (d, J=1.8 Hz, 3H). $^{13}$C NMR (125 MHz, CDCl$_3$) δ 182.12 (dd, J=3.5, 2.2 Hz), 157.71 (dd, J=246.7, 10.9 Hz), 155.24 (dd, J=252.2, 11.7 Hz), 142.39 (dd, J=11.8, 3.9 Hz), 135.17 (dd, J=8.0, 3.1 Hz), 130.56 (s), 117.01 (s), 110.97 (dd, J=23.9, 3.7 Hz), 109.32 (s), 107.69 (dd, J=26.5, 23.1 Hz), 104.94 (s), 62.23 (d, J=5.7 Hz), 37.63 (s); HRMS (EI-TOF) M$^+$ calcd for $C_{13}H_8Br_3F_2NO_2$ 484.8073, found 484.8072; HPLC purity, 100%.

Synthesis of Compound 12

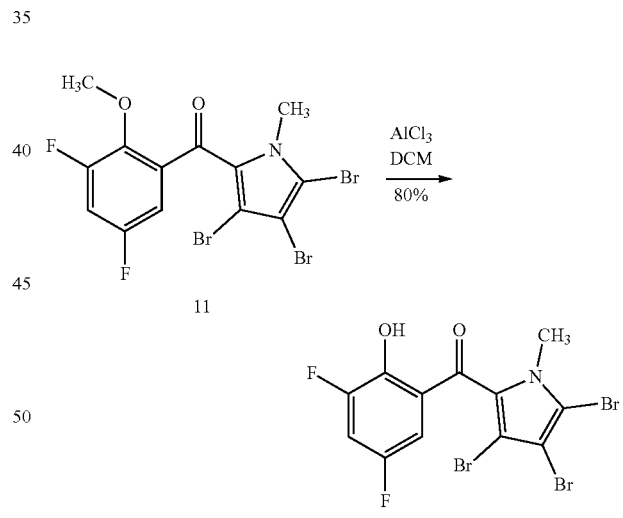

A mixture of 11 (45 mg, 0.092 mmol) and AlCl$_3$ (74 mg, 0.55 mmol) in $CH_2Cl_2$ (2 mL) was stirred at room temperature for 2 h to give compound 12 as a yellow solid (35 mg, 80%). This compound was purified by preparative HPLC. mp 156.2-157.2° C. $^1$H NMR (500 MHz, CDCl$_3$) δ 11.01 (s, 1H), 7.25-7.21 (m, 1H), 7.16 (ddd, J=10.6, 8.0, 2.9 Hz, 1H), 3.79 (s, 3H); $^{13}$C NMR (125 MHz, CDCl$_3$) δ 188.45 (t, J=3.0 Hz), 153.56 (dd, J=241.7, 10.1 Hz), 151.31 (dd, J=251.4, 11.2 Hz), 147.50 (dd, J=12.7, 2.9 Hz), 129.55 (s), 120.20 (dd, J=7.8, 3.8 Hz), 114.46 (s), 114.24 (dd, J=23.8, 4.1 Hz), 111.57 (dd, J=27.2, 21.2 Hz), 106.09 (s), 104.33 (s), 36.53 (s); HRMS (EI-TOF) M+ calcd for $C_{12}H_6Br_3F_2NO_2$ 470.7917, found 470.7914; HPLC purity, 100%.

Synthesis of Compounds 15 and 16

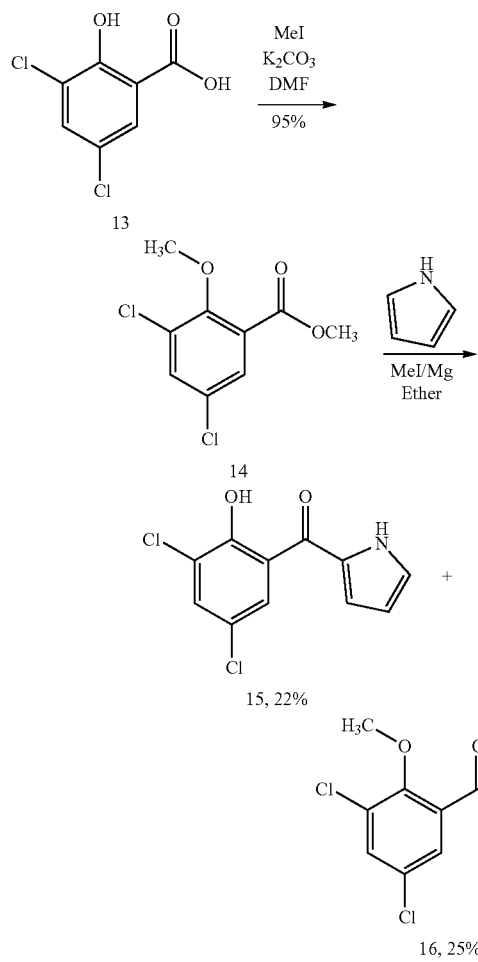

Compound 16.

Step A: To a solution of 3,5-dichlorosalicylic acid (13, 20.0 g, 0.097 mol) in DMF (150 mL) on an ice water bath were added $K_2CO_3$ (32.0 g, 0.232 mol) and iodomethane (24.0 mL, 0.384 mol). The resulting mixture was stirred at room temperature for 24 h, and evaporated to dryness. The residue was partitioned between ether and water. The organic layer was washed with 1N NaOH solution and brine, dried over anhydrous $MgSO_4$, filtered and evaporated to afford the desired product 14 as a white solid (21.6 g, 95%). $^1$H NMR (500 MHz, CDCl$_3$) δ 7.68 (d, J=2.7 Hz, 1H), 7.54 (d, J=2.7 Hz, 1H), 3.93 (s, 3H), 3.92 (s, 3H). Step B: A solution of $CH_3I$ (1.33 mL, 21.3 mmol) in ether (10 mL) was added dropwise to a stirred magnesium turning (0.51 g, 21.2 mmol) in ether (5 mL) to maintain a gentle reflux. After stirred for 0.5 h at room temperature, pyrrole (1.50 mL, 21.6 mmol) was added dropwise to maintain a gentle reflux. The resulting mixture was refluxed for 0.5 h and cooled to room temperature. To the pyrrylmagnesium iodide solution was added dropwise the solution of 14 (2 g, 8.5 mmol) in ether (40 mL). After stirred at room temperature for 2 h, the reaction mixture was quenched with saturated $NH_4Cl$ solution and extracted with ether. The organic layer was washed with brine, dried over anhydrous $MgSO_4$, filtered and evaporated. The residue was purified by silica gel column chromatography (9% ethyl acetate in hexane) to afford the desired product 16 as a brown solid (0.58 g, 25%). $^1$H NMR (500 MHz, CDCl$_3$) δ 9.45 (br s, 1H), 7.51 (d, J=2.6 Hz, 1H), 7.33 (d, J=2.5 Hz, 1H), 7.19-7.15 (m, 1H), 6.71-6.67 (m, 1H), 6.37-6.29 (m, 1H), 3.85 (s, 3H).

Compound 15.

After silica gel column purification of the reaction mixture above, a demethylated byproduct 7 was obtained as a yellow solid (0.5 g, 22%). mp 158.0-159.0° C. $^1$H NMR (500 MHz, CDCl$_3$) δ 12.27 (s, 1H), 9.56 (br s, 1H), 7.96 (d, J=2.5 Hz, 1H), 7.58 (d, J=2.4 Hz, 1H), 7.26-7.21 (m, 1H), 7.13-7.08 (m, 1H), 6.48-6.42 (m, 1H); HRMS (EI-TOF) M+ calcd for $C_{11}H_7Cl_2NO_2$ 254.9854, found 254.9862; HPLC purity, 98.5%. Synthesis of Compound 17

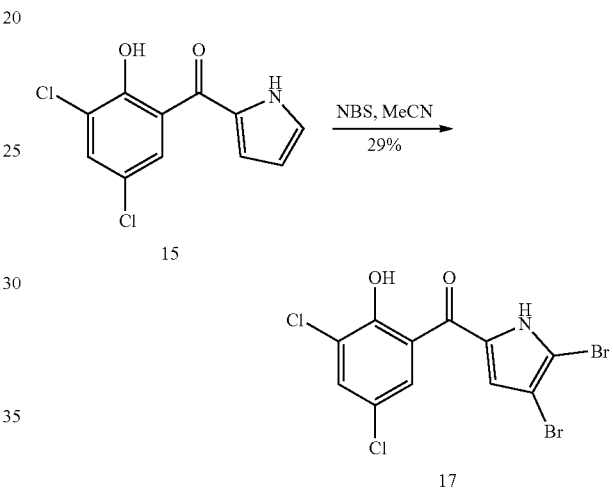

To a stirred solution of 15 (30 mg, 0.12 mmol) in $CH_3CN$ (1.0 mL) was added a solution of NBS (63 mg, 0.35 mmol) in $CH_3CN$ (0.5 mL) dropwise on an ice water bath under argon atmosphere. The resulting mixture was stirred at room temperature for 40 h. The precipitate was collected by filtration and washed with ice-cold $CH_3CN$ to give 17 as a yellow solid (15 mg, 29%). This compound was purified by preparative HPLC. $^1$H NMR (500 MHz, CDCl$_3$) δ 11.88 (s, 1H), 9.64 (s, 1H), 7.82 (d, J=2.5 Hz, 1H), 7.61 (d, J=2.4 Hz, 1H), 7.05 (d, J=2.9 Hz, 1H); HRMS (EI-TOF) M+ calcd for $C_{11}H_5Br_2Cl_2NO_2$ 410.8064, found 410.8065; HPLC purity, 100%.

Synthesis of Compound 17

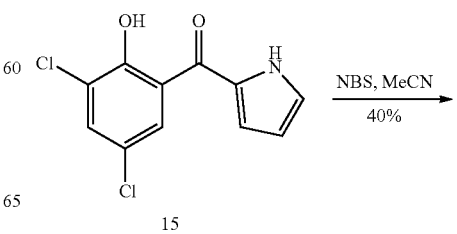

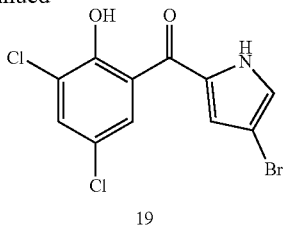

19

To a stirred solution of 15 (100 mg, 0.4 mmol) in $CH_3CN$ (5.0 mL) was added a solution of NBS (71.2 mg, 0.4 mmol) in $CH_3CN$ (1 mL) dropwise on an ice water bath under argon atmosphere. The resulting mixture was stirred at room temperature for 4 h. The precipitate was collected by filtration and washed with ice-cold $CH_3CN$ to give 19 as a yellow solid (52.8 mg, 40%). This compound was purified by preparative HPLC. mp 222.2-223.1° C. $^1$H NMR (500 MHz, Acetone-$d_6$) δ 11.89 (s, 1H), 11.70 (s, 1H), 7.98 (d, J=2.5 Hz, 1H), 7.75 (d, J=2.5 Hz, 1H), 7.49 (dd, J=3.1, 1.3 Hz, 1H), 7.25 (s, 1H). $^{13}$C NMR (125 MHz, Acetone-$d_6$) δ 184.90 (s), 156.82 (s), 135.12 (s), 130.49 (s), 129.81 (s), 128.31 (s), 124.29 (s), 124.06 (s), 122.47 (s), 122.08 (s), 99.20 (s). HRMS (EI-TOF) M$^+$ calcd for $C_{11}H_6BrCl_2NO_2$ 332.8959, found 332.8957; HPLC purity: 100%.

Synthesis of Compounds 4 and 18

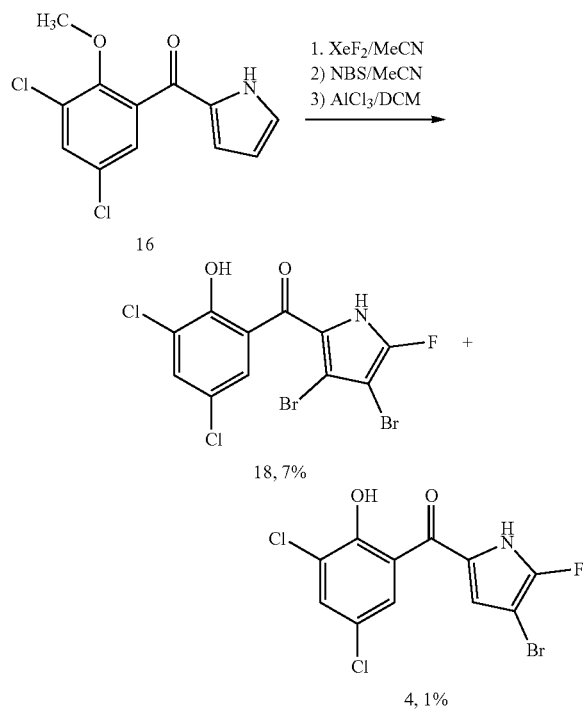

Compound 18.

To a stirred solution of 16 (1.0 g, 3.7 mmol) in $CH_3CN$ (20 mL) on an ice water bath were added $XeF_2$ (1.0 g, 5.9 mmol) under argon atmosphere. The resulting mixture was heated to 30° C. for 48 h, and then evaporated to dryness. The residue was treated with NBS (1.3 g, 7.4 mmol) followed by $AlCl_3$ (1.98 g, 14.8 mmol). After flash chromatography (silica gel/2%-9% ethyl acetate in hexane and purification by preparative HPLC, 111 mg of 18 (7%) was obtained. mp 171.9-172.7° C. $^1$H NMR (500 MHz, CDCl$_3$) δ 10.51 (s, 1H), 9.31 (s, 1H), 7.73 (d, J=2.5 Hz, 1H), 7.59 (d, J=2.4 Hz, 1H); $^{13}$C NMR (125 MHz, CDCl$_3$) δ 184.84 (s), 154.83 (s), 148.22 (d, J=274.6 Hz), 135.30 (s), 130.93 (s), 124.06 (s), 123.47 (s), 120.57 (s), 119.79 (s), 108.98 (s), 84.63 (d, J=14.0 Hz); HRMS (EI-TOF) M$^+$ calcd for $C_{11}H_4Br_2Cl_2FNO_2$ 428.7970, found 428.7962; HPLC purity, 97.8%.

Compound 4.

Same as above, after flash chromatography (silica gel/ 2%-9% ethyl acetate in hexane and purification by preparative HPLC, 13 mg of 4 (1%) was obtained. mp 207.7-208.9° C. $^1$H NMR (500 MHz, Acetone-$d_6$) δ 12.23 (s, 1H), 11.69 (s, 1H), 7.92 (d, J=2.5 Hz, 1H), 7.71 (d, J=2.5 Hz, 1H), 7.23 (d, J=4.3 Hz, 1H); $^{13}$C NMR (125 MHz, Acetone-$d_6$) δ 184.24 (d, J=3.0 Hz), 156.45 (s), 150.90 (d, J=269.4 Hz), 135.06 (s), 129.78 (s), 124.49 (s), 124.17 (s), 122.69 (s), 122.63 (s), 122.09 (s), 78.48 (d, J=14.9 Hz); HRMS (EI-TOF) M$^+$ calcd for $C_{11}H_5BrCl_2FNO_2$ 350.8865, found 350.8853; HPLC purity, 100%.

Example 2

General Procedures

Mammalian Cytotoxicity Assays.

HeLa (ATCC, Manassas, Va., USA) cells were cultured in 96-well plates at a density of 2×10$^4$ cells/well in Dulbecco's modified Eagles medium (DMEM, GIBCO Invitrogen Corp, Carlsbad, Calif.) with 10% heat inactivated fetal bovine serum (FBS) (GIBCO) and an antibiotic mixture containing penicillin and streptomycin (Life Technologies, Grand Island, N.Y.). Cells were treated with various concentrations of the PL compounds for 24 h in growth medium. Cell viability was determined by a colorimetric CellTiter 96® AQueous One Solution Cell Proliferation Assay (Promega, Madison, Wis.) based on the manufacture's instruction. Data were recorded at the absorbance of 490 nm. Each condition was tested in triplicate. The results are shown in Table 1.

Minimum Inhibitory Concentration Assays.

Broth microdilution assays were performed as described in the third edition of the ASM Clinical Microbiology Procedures Handbook. Briefly, serial 2-fold dilutions of pyrrolomycins were made in Muller Hinton II broth (cation-adjusted)(CAMHB) (Becton, Dickinson and Company, Sparks, Md.), containing 1%-5% DMSO in Costar 96-well microtiter plates (Corning, Kennebunk, Me.). Bacterial cultures were prepared using the direct colony suspension method to 0.5 McFarland units and each well was inoculated with 10 μL of this suspension. Plates were incubated statically at 37° C. for 20-24 h. MIC values were reported as the lowest concentration of antibiotic in which no growth was seen.

Minimum Bactericidal Concentration Assays.

MBC assays were performed according to a published protocol.[33] Overnight cultures grown in CAMHB were adjusted to an OD$_{600}$ of 0.05 in 25 mL of CAMHB in a 250-mL flask. They were then allowed to grow at 37° C. with agitation at 250 rpm to exponential phase (OD$_{600}$=0.5) at which point the cultures were diluted to achieve a concentration of 5×10$^6$ cfu/mL. One hundred microliters of the diluted, exponential phase bacteria were added to 1 mL of the pyrrolomycins, and control antibiotics, vancomycin and ciprofloxacin for SA and BA, respectively, in a 10-mL tube. Bacteria were harvested at 0, 1, 3 and 24 h and plated for viable cell counts and reported as cfu/mL.

Anti-Staphylococcal Biofilm Activity.

Static biofilms were generated using a published protocol. Briefly, overnight cultures of *S. aureus* were diluted to an $OD_{600}$ of 0.05 in TSB-NaCl/Glc, and 200 μL was inoculated into wells of a Costar 3596 plate (Corning life Sciences, Acton, Mass.), that had been coated overnight at 4° C. with 20% human plasma (Sigma). After 24 h of static growth, at 37° C. the biofilms were washed two times with PBS and the remaining biofilm was treated with pyrrolomycin derivatives in Muller Hinton II broth (cation-adjusted) (Becton, Dickinson and Company, Sparks, Md.) supplemented with 5% DMSO (Sigma). After 24, 48 or 120 h of treatment, the remaining biofilm was washed two times with PBS and then re-suspended in 100 μL PBS, serial diluted and plated for cfu.

Pharmacokinetics of Pyrrolomycin 4.

A Waters ACQUITY ultra-performance liquid chromatography (UPLC) system (Waters, Milford, Mass.) coupled to a 4000 Q TRAP® quadrupole linear ion trap hybrid mass spectrometer with an electrospray ionization (ESI) source (Applied Biosystems, MDS Sciex, Foster City, Calif.) was used throughout. All chromatographic separations were performed with an ACQUITY UPLC® BEH Shield RP18 column (2.1×100 mm, 1.7 μm; Waters) equipped with an ACQUITY UPLC $C_{18}$ guard column (Waters, Milford, Mass.). Mobile phase A consisted of 0.1% acetic acid and mobile phase B was methanol (MeOH). The initial mobile phase composition was 80% B for the first 3 min and was gradually increased to 95% B in 4.25 min and held constant for 1.25 min. Mobile phase B was then reset to 80% in 0.25 min and the column was equilibrated for 1 min before the next injection. A flow rate of 0.25 mL/min was used and the injection volume of all samples was 10 μL. MS/MS analyses were performed with negative ESI mode and using the following parameters: ion spray voltage, −4500 V; source temperature, 500° C.; curtain gas (nitrogen), 10 arbitrary units; and collision gas (nitrogen), "High". Specific detection was performed by monitoring the transition 349.67→160.8 m/z for 4. In addition, for the detection of potential 4 metabolites, multiple reaction monitoring-information-dependent acquisition-enhanced product ion, neutral loss, precursor ion and enhanced MS scans were used as described previously.[37-40]

Plasma samples were prepared by protein precipitation using ice-cold methanol. Sixty-five μL of methanol was added to 25 μL plasma samples pre-spiked with 10 μL of internal standard (500 ng/ml). Samples were then vortexed, and centrifuged at 16,000×g for 10 min. After centrifugation at 16,000×g for 10 min, 80 μL supernatant were mixed with 40 mL of 10% methanol in $H_2O$. Further, 10 μL of each sample was used for LC-MS/MS analysis.

Eight-week-old healthy male Balc/c mice were purchased from Charles River Laboratories. Sterilized 7012 Teklad diets (Harlan) were used for mice, and water was provided ad libitum. A 10 mg/kg oral dose was administered as 250 μL of solution (4, 1 mg/mL) in a mixture of DMSO-PEG400-PG-EtOH-Cremophore-PBS (2/20/10/10/5/53% v/v) to a 25 g mouse. A 1.0 mg/kg intravenous dose was administered as a 100 μL of solution (4, 0.25 mg/mL) in the same DMSO-$PEG_{400}$-PG-EtOH-Cremophore-PBS mixture to a 25 g mouse. Oral doses were administered via oral gavage, whereas intravenous doses were administered via the tail vein. Blood samples were collected at 0, 5, 15, 30, 45 min, and 1, 2, 4, 8, 24, 48, and 72 h post oral administration, and at 0, 5, 30 min, and 1, 3, 8, 24, 48, and 72 h post intravenous dosing. Plasma was separated by centrifugation of blood samples at 2000×g for 5 min at 4° C. within 1 h of sample collection. The pharmacokinetic parameters were determined using the noncompartmental analysis module of WinNonlin (version 5.1, Pharsight, Mountain View, Calif.). The absolute bioavailability (F) was calculated as the ratio between the $AUC_{0\text{-}infinity}$ from oral and intravenous routes, after dose normalization using the following equation:

$$\% F_{Absolute} = \frac{AUC_{Oral} \times Dose_{i.v.}}{AUC_{i.v.} \times Dose_{oral}} \times 100$$

Results and Discussion

Mammalian cytotoxicity was determined for all active pyrrolomycins with MIC values <0.20 μg/mL using human Hela cells (Table 1). Selectivity Index (SI) was defined as a ratio of $IC_{50}$ of human Hela cytotoxicity/MIC against either BA or SA (both in [temL). Pyrrolomycins 3 and 4 had SI values of >1,484 and >751 against BA and >275 and >484 against SA, respectively, demonstrating that they are selective antibacterial agents without toxicity at concentrations several hundred to a thousand-fold higher than their MICs. The Ligand Efficiency (LE) of each compound was calculated to determine the binding energy per non-hydrogen atom of a ligand to its binding partner.[34,35] LE is used as a parameter for optimization of both physicochemical properties and pharmacological properties.[36]

Figure 2:
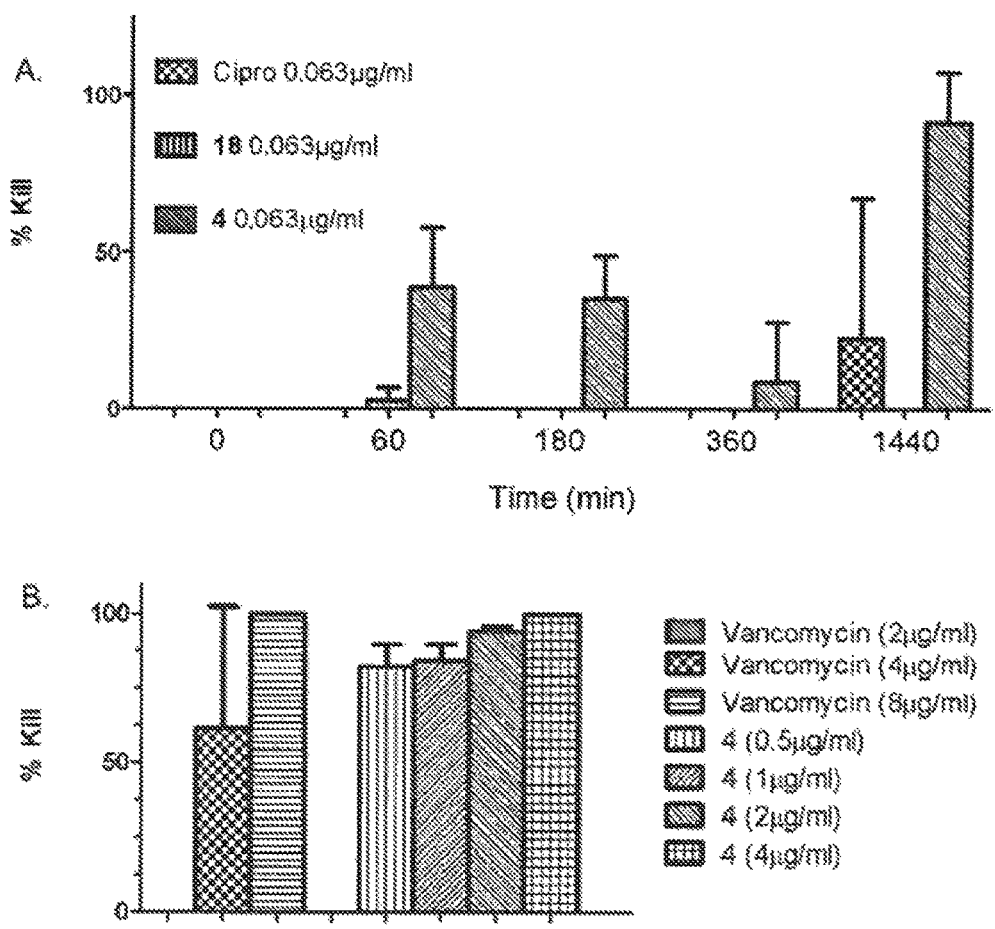
FIG. 2 shows (A) the bactericidal activity of pyrrolomycins 4 and 18 against *Bacillus anthracis*, compared with that of ciprofloxacin, after 1 h, 3 h, 6 h, and 24 h periods; and (B) the bactericidal activity of pyrrolomycins 4 and 18 against *Staphylococcus aureus* compared with that of vancomycin.

The bactericidal activities of pyrrolomycins 4 and 18 were compared with that of ciprofloxacin against BA for a period of 24 hours (FIG. 2A). Compound 4 reduces BA culture viability by 60% in 60 minutes and compound 18 reduces viability by 92%, while ciprofloxacin fails to kill BA at the same concentration of 0.063 μg/mL. In 24 h, compound 4 reduces BA culture viability by 99.9% but ciprofloxacin reduces viability by only 30%. For compound 4 against SA at a concentration of 4 μg/mL, 100% killing was observed with no growth of colonies after incubation for 48 hours (FIG. 2B).

Figure 3:
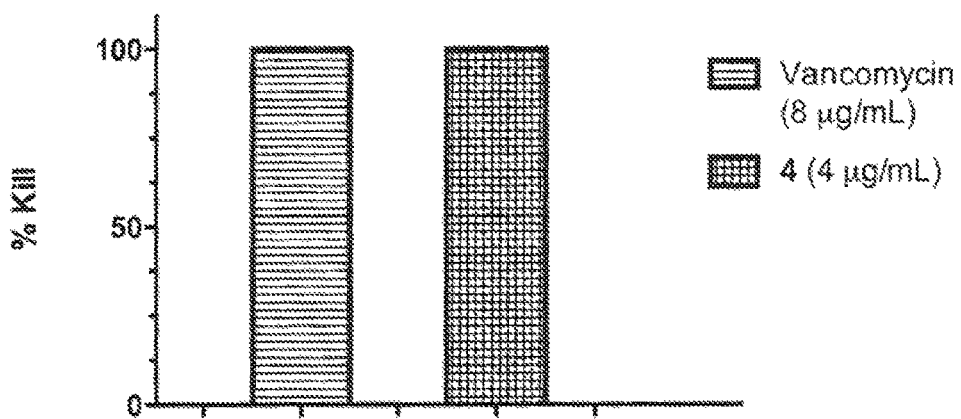
FIG. 3 shows the minimum bactericidal concentration of pyrrolomycin 4 against *Staphylococcus aureus* after 24 h compared with that of vancomycin.
Figure 4:
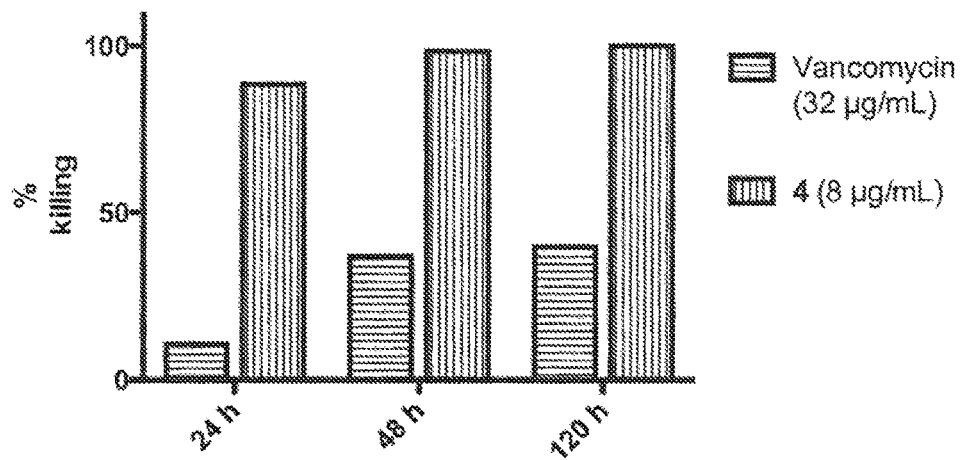
FIG. 4 shows the anti-biofilm activity of pyrrolomycin 4 against *Staphylococcus aureus* compared with that of vancomycin after 24 h, 48 h, and 120 h.

The results show that the MBC value of pyrrolomycin 4 is 4 μg/mL in 24 hours while 100% killing of SA requires 8 μg/mL of vancomycin (FIG. 3, n=4). As shown in FIG. 4 (n=4), compound 4 kills 84% biofilms in 24 hours at a concentration of 8.0 μg/mL, while vancomycin kills only 11% at 32 μg/mL. Compound 4 continues to achieve 97% biofilm killing at the corresponding concentration in 48 hours. In 120 hours, pyrrolomycin 4 kills >99.9% biofilms at 8.0 μg/mL, while vancomycin kills only 39% at 32 μg/mL. Compound 4 disrupts pre-formed biofilms at the concentration of 8.0 μg/mL in five days.

Compounds 1-4, 8-12, 15, 17, and 18 were evaluated for their ability to inhibit growth of BA, SA (Table 1), and other Gram-positive pathogens including *E. faecium*, vancomycin-resistant *Enterococcus* and methicillin-resistant *S. epidermidis*. Gram-negative ESKAPE pathogens, including *Klebsiella pneumonia*, *Acinetobacter baumannii*, *Pseudomonas aeruginosa* and *Enterobacter* spp were also evaluated. Although some derivatives were found to have a broad spectrum of activity against Gram-negative pathogens, the compounds reported here exhibited the most pronounced inhibitory activity against Gram-positive bacteria.

Structure-Activity Relationship (SAR)—*Bacillus anthracis*.

Marinopyrrole derivative 1 is as potent as ciprofloxacin against BA with an MIC value of 0.063 μg/mL. Marinopyrrole 2 is two-fold less potent than ciprofloxacin with an MIC of 0.125 μg/mL. Importantly, it was determined that both pyrrolomycins 3 and 4, which are fragments of marinopyrrole, exhibited higher potency than the marinopyrroles with MIC values of 0.031 µg/mL and 0.047 µg/mL, respectively. More significantly, these novel fluorinated pyrrolomycins 3 and 4 are the most efficient binders that have ever been reported as anti-BA agents with LEs of 0.60 and 0.59, respectively (Table 1). A four-fold increase in anti-BA activity was observed upon replacing bromine with fluorine, as exhibited by 4 and 17 with MIC values of 0.047 µg/mL and 0.188 µg/mL, respectively (Table 1). Dibromo congener 18, with an extra bromine substituted in the pyrrole ring, is not only three-fold less potent (MIC=0.125 µg/mL) than 4, but also has a c log P value that is almost a full log unit higher (Table 1). Compound 4 has a c log P of 4.1 and the c log P values of 17 and 18 are 4.7 and 4.9, respectively. In general, more lipophilic compounds possess more potent antibacterial activity. This finding demonstrated that the least lipophilic compound 4 exhibited the most potent anti-potent than 3. Both 11 and 12 are 24-fold less active than 3. These results suggest that neither the pyrrole nitrogen nor the hydroxyl group in the benzene ring can be substituted to achieve potent anti-SA activity.

Pharmacokinetics of Pyrrolomycin 4.

Figure 5:
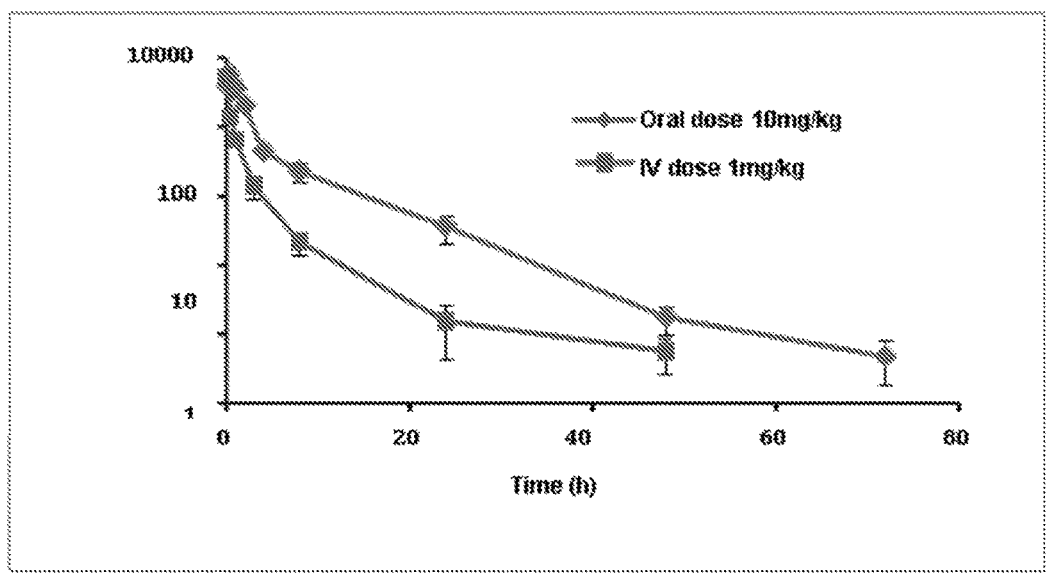
FIG. 5 shows the plasma concentration of pyrrolomycin 4 in mice after oral administration as a function of time.

A sensitive and specific LC-MS/MS method has been developed for determination of 4 in mouse plasma.[37-40] Following intravenous (IV) and oral dosing in mice, the oral bioavailability of 4 was found to be 35%. The compound was well absorbed with maximum plasma concentration ($C_{max}$) observed after 0.25 h of oral administration. The elimination half-life was 6.04 hours and 6.75 hours following IV and oral administration, respectively. The AUC for the IV dose at 1 mg/kg was 3.8 µg*h/mL and 13.2 µg*h/mL for the oral dose at 10 mg/kg, respectively. The plasma concentrations vs. time profiles after IV and oral administration of 4 in mice are shown in FIG. 5. After both IV and oral administration, parent compound 4 was detectable in plasma up to 72 hours with the detection limit of 0.8 ng/mL.

TABLE 1

| Compound ID | clogP[a] | MIC[b] BA | LE[c] BA | MIC[d] SA | LE SA | $IC_{50}$[e] | SI BA | SI[f] SA |
|---|---|---|---|---|---|---|---|---|
| 1 | 6.5 | 0.063 | 0.30 | 0.078 | 0.29 | >40.9 | >649 | >524 |
| 2 | 6.1 | 0.125 | 0.29 | 0.19 | 0.28 | >52.8 | >422 | >280 |
| 3 | 5.5 | 0.031 | 0.60 | 0.17 | 0.54 | >46.0 | >1484 | >275 |
| 4 | 4.1 | 0.047 | 0.59 | 0.073 | 0.57 | >35.3 | >751 | >484 |
| 8 | 2.1 | >4.0 | ND | >4.0 | ND | ND | ND | ND |
| 9 | 2.7 | >4.0 | ND | >4.0 | ND | ND | ND | ND |
| 10 | 4.1 | 1.5 | ND | 3.0 | ND | ND | ND | ND |
| 11 | 4.3 | >4.0 | ND | >4.0 | ND | ND | ND | ND |
| 12 | 5.0 | >4.0 | ND | >4.0 | ND | ND | ND | ND |
| 15 | 3.4 | >4.0[g] | ND | >4.0[e] | ND[f] | ND | ND | ND |
| 17 | 4.7 | 0.188 | 0.50 | 0.073 | 0.54 | >41.4 | >220 | >567 |
| 18 | 4.9 | 0.125 | 0.51 | 0.19 | 0.51 | >43.2 | >346 | >229 |
| 19 | 4.2 | ND[h] | ND | >4.0 | ND | ND | ND | ND |

[a]Calculated using ChemAxon MarvinSketch version 15.7.6.0, Hungary;
[b]MIC: Minimum Inhibitory Concentration of pyrrolomycin in µg/mL against *Bacillus anthracis* $V_{770}$-$NP_1$-R (n ≥ 3) with ciprofloxacin as a positive control (MIC = 0.063 µg/mL);
[c]LE: Ligand Efficiency ≈ −ΔG/HAC, defined as the free energy of binding divided by the number of non-hydrogen atoms (Heavy Atom Count);
[d]MIC: Minimum Inhibitory Concentration of pyrrolomycin in µg/mL against *Staphyloccocus aureus* $USA_{300}$ (n ≥ 3) with vancomycin as a positive control (MIC = 2.0 µg/mL);
[e]$IC_{50}$: Concentration of the pyrrolomycin in µg/mL at which the human Hela cell proliferation was inhibited by 50% with respect to the untreated growth control, the highest concentration tested was 100 µM;
[f]SI: Selectivi Index was defined as a ratio of $IC_{50}$ of human Hela cell cytotoxicity to MIC;
[g]Highest concentration tested was 4 µg/mL;
[h]ND: not determined.

bacterial activity. The most potent pyrrolomycin is 3 with fluorine substitutions on both para- and ortho positions of the benzene ring. This further reinforced the idea that introducing fluorine atoms into pyrrolomycin not only increased the potency but also improved the physicochemical and drug-like properties of this compound.

SAR—*Staphylococcus aureus*.

Pyrrolomycins 4 and 17 are equally potent against SA, with MIC values of 0.073 µg/mL similar to that of marinopyrrole 1 although the LE values of the former almost twice that of the latter (see Table 2). Compounds 4 and 5 have the same anti-staphylococcal activity while their structures differ by only one atom (fluorine vs. bromine) at the A position. Compound 19 (A=CH) is at least 54-fold (MIC>4.0 µg/mL) less active than its fluorine or bromine congeners 4 and 17 (Table 1). Although there is no obvious fluorine effect on anti-staphylococcal activity (MIC) observed between compound 4 and 17, they do have different bactericidal activities. Compounds 15 and 9 are 21-57-fold less potent than compounds 4, 17, and 18, suggesting that A and D should be either CF or CBr. Compound 18 is less active than 4. Compound 10 with methyl substituted at W is 18-fold less

REFERENCES (1) Bush, et al. New England J. Med. 2001, 345, 1607-1610.
(2) Inglesby, et al. JAMA 2002, 287, 2236-2252.
(3) Williamson, and Dyson, Front. in Microb. 2015, 6, 1009.
(4) Weiss, et al. Antimicrob. Agents Chemother. 2011, 55, 1533-1542.
(5) Weigel, et al. Antimicrob. Agents Chemother. 2010, 54, 2793-2800.
(6) Brook, et al. Int. J. Antimicrob. Agents 2001, 18, 559-562.
(7) Choe, et al. Antimicrob. Agents Chemother. 2000, 44, 1766.
(8) Price, et al. Antimicrob. Agents Chemother. 2003, 47, 2362-2365.
(9) Chambers, et al. Nat. Rev. Microbiol. 2009, 7, 629-641.
(10) Jarvis, et al. Am. J. Infect. Control 2012, 40, 194-200.
(11) Rice, et al. J. Infect. Dis. 2008/97, 1079-1081.
(12) Pendleton, et al. Expert Rev. Anti. Infect. Ther. 2013, 11, 297-308.

(13) Sheldrick, et al. Nature 1978, 271, 223-225.
(14) Hiramatsu, et al. J. Antimicrob. Chemother. 1997, 40, 135-136.
(15) Aguado, et al. Emerg. Infect. Dis. 2011, 17, 1099-1102.
(16) Dhand and Sakoulas. Fi000 Med. Rep. 2012, 4, 4.
(17) Zhao, et al. Front. Biotechnol. Pharm. 2001, 2, 329-349.
(18) Silverman, et al. J. Infect. Dis. 2005, 191, 2149-2152.
(19) Maggiore, et al. Expert Rev. Clin. Pharmacol. 2015, 8, 141-153.
(20) Morata, et al. Curr. Opin. Pharmacol. 2015, 24, 45-51.
(21) Leuthner, et al. Expert Rev. Anti. Infect. Ther. 2015, 13, 149-159.
(22) Dolgin, et al. Nature Med. 2010, 16, 1054.
(23) Liu, et al. Mar. Drugs 2012, 10, 953-962.
(24) Liu, et al. Mar. Drugs 2014, 12, 2458-2470.
(25) Li. Med. Res. Rev. 2016, 36, 169-189.
(26) Lipinski, et al. Adv. Drug Deily. Rev. 2001, 46, 3-26.
(27) Baell and Holloway. J. Med. Chem. 2010, 53, 2719-2740.
(28) Dalvie, et al. Chem. Res. Toxicol. 2002, 15, 269-299.
(29) Hagmann. J. Med. Chem. 2008, 51, 4359-4369.
(30) Muller, et al. Science 2007, 317, 1881-1886.
(31) Gillis, et al. J. Med. Chem. 2015, 58, 8315-8359.
(32) Umezu, et al. J. Fluor. Chem. 2003, 121, 97-99.
(33) Suarez, et al. Antimicrob. Agents Chemother. 2005, 49, 3847-3857.
(34) Kuntz, et al. Proc. Natl. Acad. Sci. U.S.A. 1999, 96, 9997-10002.
(35) Hajduk. J. Med. Chem. 2006, 49, 6972-6976.
(36) Abad-Zapatero and Metz. Drug Discov. Today 2005, to, 464-469.
(37) N. Gautam et al. Biomed Chromatogr, 27 (2013) 900-909.
(38) N. Gautam et al. Xenobiotica, (2015) 1-16.
(39) J. Huang et al. Drug Metab Pharmacokinet, 25 (2010) 487-499.
(40) J. Huang et al. Xenobiotica, 40 (2010) 184-194.

What is claimed is:

1. A compound, or pharmaceutically acceptable salt thereof, having a structure of formula (I):

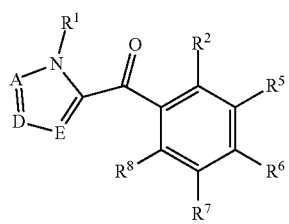

(I)

wherein
R$^1$ is H, C$_{1-10}$alkyl, or COR$^9$;
R$^2$ is OH, C$_{1-10}$alkoxy, NHC(O)R$^9$, or NHSO$_2$R$^{10}$;
A, D, and E are selected as indicated in one of groups (i)-(iv):
 (i) A and D are each independently CR$^3$ and E is N;
 (ii) A is CR$^3$, D is N, and E is CH;
 (iii) A is CR$^3$, and D and E are each N; and
 (iv) A is N, D is CR$^3$, and E is CH
each R$^3$ is H, halogen, C$_{1-10}$haloalkyl, C$_{1-10}$haloalkoxy, CN, CONHR$^9$, SO$_2$R$^{10}$, or SO$_2$NHR$^9$;
R$^5$ is F or Cl;
R$^6$, R$^7$, and R$^8$ are each H, halogen, CF$_3$, or OCF$_3$;
R$^9$ is H, C$_{1-10}$alkyl, or C$_{6-10}$aryl; and
R$^{10}$ is C$_{1-10}$alkyl or C$_{6-10}$aryl,
with the proviso that at least one R$^3$ is other than H, and at least one of R$^5$, R$^6$, R$^7$, and R$^8$ is other than H.

2. The compound or salt of claim 1, wherein A and D are each CR$^3$, and E is N.

3. The compound or salt of claim 1, wherein A is CR$^3$, D is N, and E is CR$^4$.

4. The compound or salt of claim 1, wherein A is CR$^3$, and D and E are N.

5. The compound or salt of claim 1, wherein A is N, D is CR$^3$, and E is CR$^4$.

6. The compound or salt of claim 1, wherein R$^3$ is halogen, CF$_3$, OCF$_3$, CN, CONHR$^9$, SO$_2$R$^{10}$, or SO$_2$NHR$^9$.

7. The compound or salt of claim 1, wherein R$^2$ is NHC(O)R$^9$, or NHSO$_2$R$^{10}$.

8. The compound or salt of claim 1, wherein R$^1$ is H or C$_{1-10}$alkyl.

9. The compound or salt of claim 1, wherein R$^6$ and R$^8$ are each independently F or Cl.

10. A compound or pharmaceutically acceptable salt thereof having a structure selected from the group consisting of:

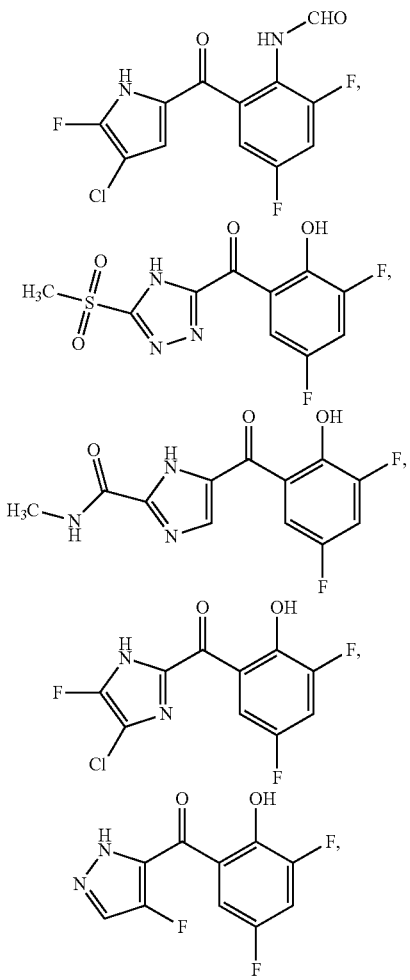

-continued

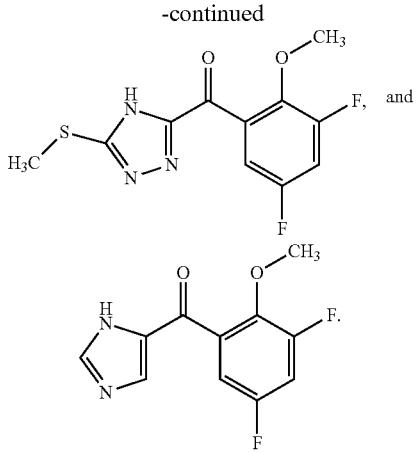

11. A method of inhibiting the growth or proliferation of bacteria or pathogen in a subject, comprising contacting the bacteria with the compound or salt of claim 1, wherein the bacteria or pathogen is *Staphylococcus, Enterococcus, Bacillus, Streptococcus, Klebsiella, Acinetobacter, Pseudomonas, Enterobacter, Escherichia, Clostridium, Citrobacter, Serratia, Neisseria, Corynebacterium, Cyanobacterium, Salmonella, Shigella, Helicobacter, Brucella, Borrelia, Bordetella, Bartonella, Bacteroides, Burkholderia, Mycobacterium, Mycoplasma, Campylobacter, Chlamydia, Chlamydophila, Francisella, Haemophilus, Legionella, Leptospira, Listeria, Rickettsia, Vibrio, Ureaplasma, Yersinia, Treponema, Proteus, Stenotrophomonas, Plesiomonas, Nocardia, Actinomyces, Moraxella, Erysipelothrix, Actinobacillus, Anaplasma, Pasteurella, Alcaligenes, Achromobacter,* or *Candida*.

12. The method of claim 11, wherein the pathogen or bacteria is methicillin-resistant, carbapenem-resistant, fluoroquinone-resistant, vancomycin-resistant, or multidrug-resistant.

13. The compound or salt of claim 1, wherein $R^7$ is F or Cl.

14. The compound or salt of claim 1, wherein $R^6$ and $R^8$ are each H.

* * * * *